(12) United States Patent
Olivas et al.

(10) Patent No.: US 6,492,579 B2
(45) Date of Patent: Dec. 10, 2002

(54) LETTUCE VARIETY LEGEND

(75) Inventors: Nathan K. Olivas, Salinas, CA (US); Nathan J. Olivas, Salinas, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 09/862,201

(22) Filed: May 21, 2001

(65) Prior Publication Data

US 2002/0104129 A1 Aug. 1, 2002

Related U.S. Application Data

(60) Provisional application No. 60/206,549, filed on May 24, 2000.

(51) Int. Cl.[7] ............................. A01H 4/00; A01H 1/00; A01H 5/00; A01H 5/10; A01H 5/12

(52) U.S. Cl. ........................ 800/305; 800/260; 800/265; 800/295; 800/298; 435/410; 435/430.1

(58) Field of Search ................................. 800/305, 260, 800/265, 295, 298; 435/410, 430.1

(56) References Cited

PUBLICATIONS

Ryder et al. 1991. 'Pacific' Lettuce. Hortscience 26(4):437–438.*

* cited by examiner

*Primary Examiner*—David T. Fox
*Assistant Examiner*—Francis Moonan
(74) *Attorney, Agent, or Firm*—Morrison & Foerster LLP

(57) ABSTRACT

A new lettuce variety designated Legend is described. Legend is an iceberg lettuce variety exhibiting stability and uniformity. Legend lettuce seeds are deposited with the American Type Culture Collection and have ATCC deposit number PTA-4009.

7 Claims, 1 Drawing Sheet

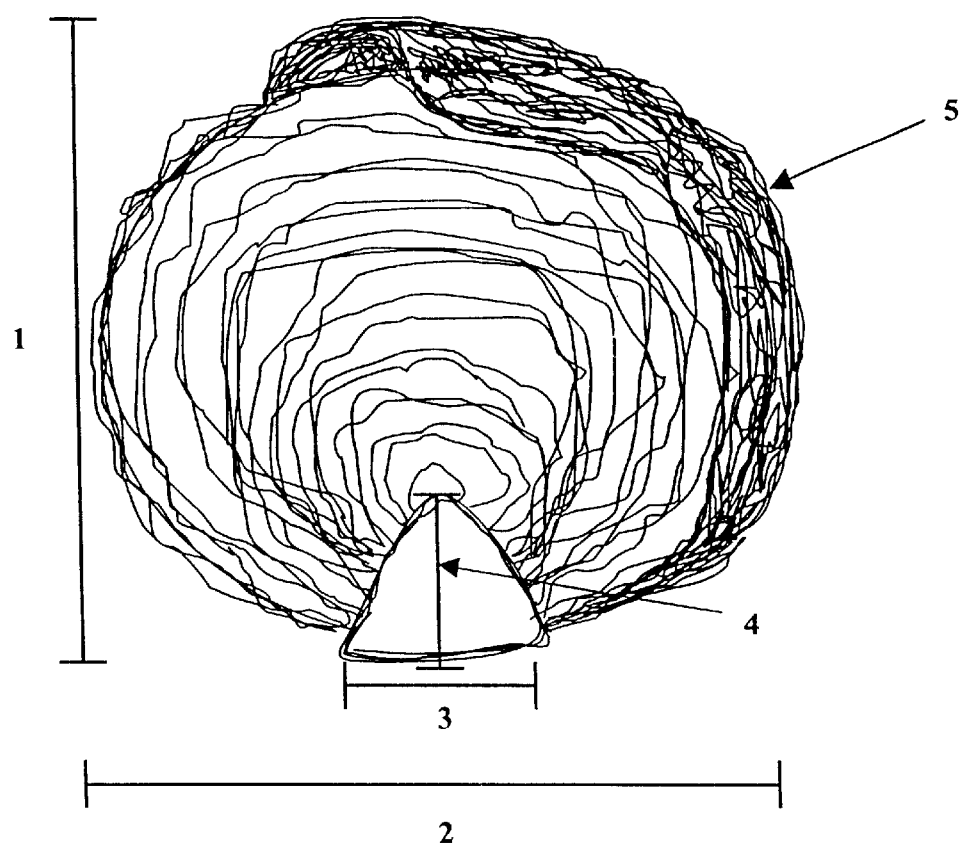
FIGURE 1: Sliced Iceberg Lettuce

LETTUCE VARIETY LEGEND

I. RELATED APPLICATION

This application claims the benefit under 35 U.S.C. § 119(e) of U.S. provisional patent application No. 60/206,549 filed May 24, 2000 which is hereby incorporated by reference in its entirety.

II. FIELD OF THE INVENTION

This invention relates to the field of plant breeding. In particular, this invention relates to a new lettuce, *Lactuca sativa*, variety, Legend.

III. BACKGROUND OF THE INVENTION

Lettuce is an increasingly popular crop. Worldwide lettuce consumption continues to increase. As a result of this demand, there is a continued need for new lettuce varieties. In particular, there is a need for improved iceberg lettuce varieties that exhibit vigorous growth, increased weight and yield.

IV. SUMMARY OF THE INVENTION

In order to meet these needs, the present invention is directed to an improved iceberg lettuce variety that exhibitsvigorous growth, increased weight and yield. In particulate, the the present invention is directed to lettuce, *Lactuca sativa*, seed designated as Legend having ATCC Accession Number PTA-4009. The present invention is further directed to a lettuce, *Lactuca sativa* plant produced by growing Legend lettuce seed having ATCC Accession Number PTA-4009. The present invention is further directed to a Lactuca sativa plant having all the physiological and morphological characteristics of a Lactuca sativa plant produced by growing Legend lettuce seed having ATCC Accession Number PTA-4009. The present invention is further directed to an $F_1$ hybrid lettuce, *Lactuca sativa* plant having Legend as a parent wherein Legend is grown from Legend lettuce seed having ATCC Accession Number PTA-4009.

The present invention is further directed to pollen and ovules isolated from Legend lettuce plants. The present invention is further directed to tissue culture of Legend lettuce plants.

The present invention is further directed to a method of selecting lettuce plants comprising a) growing Legend lettuce plants wherein the Legend plants are grown from lettuce seed having ATCC Accession Number PTA-4009 and b) selecting a progeny plant from step a) wherein the progeny plant is phenotypically distinguishable from the parent plant. The present invention is further directed to lettuce plants and seeds produced by the lettuce plants wherein the lettuce plants are isolated by the selection method of the invention.

The present invention is further directed to a method of breeding lettuce plants comprising crossing a lettuce plant with a plant grown from Legend lettuce seed having ATCC Accession Number PTA-4009. The present invention is further directed to lettuce plants and seeds produced thereform where the lettuce plant is isolated by the breeding method of the invention.

V. BRIEF DESCRIPTION OF THE DRAWING

The invention will be better understood by reference to FIG. 1 which shows a drawing of a cross-section of an iceberg lettuce head showing head length 1, head diameter 2, core diameter 3, core length 4, and a wrapper leaf 5. In the description that follows, head length, head diameter, core diameter, core length, and wrapper leaf are described without associated reference numbers, but are intended to correspond to the respective reference numbers listed above.

VI. BRIEF DESCRIPTION OF THE TABLES

The invention will be better understood by reference to the Tables in which;

Table 1 shows trial data comparing Legend and Bonanza iceberg lettuce varieties.

Table 2 shows trial data comparing Legend and Bonanza iceberg lettuce varieties.

Table 3 shows trial data comparing Legend and Bonanza iceberg lettuce varieties.

Table 4 shows trial data comparing Legend and Bonanza iceberg lettuce varieties.

Table 5 shows trial data comparing Legend and Bonanza iceberg lettuce varieties.

Table 6 shows trial data comparing Legend and Bonanza iceberg lettuce varieties.

Table 7 shows trial data comparing Legend and Pybas 251 iceberg lettuce varieties.

Table 8 shows trial data comparing Pybas 251 and Legend iceberg lettuce varieties.

Table 9 shows trial data comparing Legend and Pybas 251 iceberg Lettuce varieties.

Table 10 shows trial data comparing Legend and Pybas 251 iceberg lettuce varieties.

Table 11 shows trial data comparing Legend and Pybas 251 iceberg Lettuce Varieties.

Table 12 shows trial data comparing Sharpshooter and Legend iceberg lettuce varieties.

Table 13 shows bolting data comparing Legend, Pybas 251 and Bonanza iceberg lettuce varieties.

VII. DETAILED DESCRIPTION OF THE INVENTION

In order to more clearly understand the invention, the following definitions are provided:

Iceberg Lettuce

Iceberg lettuce, *Lactuca sativa* L. var. *capitala* L. is also known as 'crisp head' lettuce. Iceberg lettuce is a lettuce plant type that forms a firm, spherical head formed with tightly folded brittle textured foliage as illustrated in FIG. 1. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length

Core length is the length of the internal lettuce stem. Core length is measured from the base of the cut head to the tip of the core.

Core Diameter

Core diameter is the diameter of the lettuce stem at the base of the cut head.

Head Diameter

Head diameter is the diameter of the vertically sliced lettuce plant head at its widest horizontal point, perpendicular to the stem.

Head Length

Head length is the diameter of the vertically sliced lettuce plant head as measured from the base of the cut stem to the cap leaf.

Average Head Diameter

Average head diameter is an average of the measured head diameter and head length of the lettuce head.

Average Head Diameter:Core Length Ratio

The ratio of the average head diameter to core length is indicative of the percentage of useable product produced by the lettuce plant.

Frame Diameter

The frame diameter is a measurement of the lettuce plant diameter at its widest point. The measurement of frame diameter is from the outer most wrapper leaf tip to outer most wrapper leaf tip.

Head Weight

Head weight is the weight of the marketable lettuce plant, cut and trimmed to market specifications.

Rogueing

Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage

Market stage is the stage when a lettuce plant is ready for commercial lettuce harvest. In the case of an iceberg lettuce variety, a lettucehead is at market state when the head is solid and has reached an adequate size and weight.

Big Vein

Big Vein a viral disease known to infect lettuce as described in U.S. Pat. No. 5,684,226 which is hereby incorporated by reference. Resistance to big vein disease via infection through *Olpidium brassicae* refers to a level of resistance in a novel lettuce variety as measured by visual symptoms. Resistance is deemed present when symptoms are not present in at least 85% of the novel variety plants when compared to a known resistant lettuce variety growing under comparable conditions to the novel variety.

Taking into account these definitions, the present invention is directed to seeds of the lettuce variety Legend, plants produced by growing Legend lettuce seeds, one or more plants selected from a collection of Legend plants and seeds derived or produced therefrom; plants produced by crossing a lettuce plant with a Legend lettuce plant and seeds derived or produced therefrom.

VIII. ORIGIN AND BREEDING HISTORY OF THE VARIETY LEGEND

Legend is an iceberg lettuce variety developed from a hand pollinated cross of Pybas 251 available from Pybas Seed Co. and Bonanza developed by Asgrow. The two parental varieties were selected for their compatibility. Pybas 251 was selected for its large head and frame size, and Bonanza for its resistance to Big Vein. The cross was made to produce a large heading, large framed iceberg lettuce for early winter plantings in Yuma, Ariz., and mid winter and spring plantings in the Salinas Valley of California.

Approximately 40 plants of the F1 seed were planted in a San Joaquin Valley production field for seed increase in year 2. The block was rogued, eliminating the self pollinating plants. The F2 seed was harvested in August year 2.

The F2 seed was evaluated in research and development plot trials in year 3. Individual plant selections were made, the plants were removed from the field, potted, and grown to seed in a green house. Selected lines were increased in year 4 in a San Joaquin Valley production field. The blocks were intensely rogued at the market stage, and selections were made for the plants demonstrating improved head and frame size and a smoother texture. The selections were harvested individually and additional rogueing for uniformity in size and maturity was done in each block until complete seed maturity. The remaining plants were bulk harvested producing the F3 trial seed in the fall of year 4.

The F3 seed was extensively trialed throughout the year 5 and 6 growing seasons in Yuma, Ariz., and the Salinas Valley of California demonstrating the desired phenotype and good resistance to Big Vein. Seed from the F3 selections were increased in year 6 in San Joaquin Valley research production, demonstrating improved head and frame size, and a smoother texture. Further rogueing for size, type and maturity was done until harvest of the F4 seed. PX 535 was again noted to express the desired phenotypic traits.

The F4 seed was evaluated in research and development plot trials during the year 6, 7 and 8 growing seasons in the winter plantings of Yuma, Ariz., and the Salinas Valley of California, where it exhibited good uniformity, the desired phenotype and Big Vein resistance. The F4 seed was increased in the year 8 in the San Joaquin Valley research production and selectively rogued for uniformity of type, size and maturity. The F5 seed was then harvested.

During the year 9 growing season the F5 seed was trialed in Yuma, Ariz., and the Salinas Valley of California again demonstrating Big Vein resistance. This variety was noted to exhibit the desired phenotypic traits, producing an improved head and frame size, while being uniform, stable and without variants. The F5 seed was planted in year 9 in a San Joaquin Valley commercial production field where it was selectively rogued for uniformity in size and maturity. The F6 seed was harvested.

As evaluated in seed production and field trials the F5 and F6 seed from the variety Legend has been uniform and stable with out variants.

*Lactuca sativa* cultivar Legend has numerous distinguishing characteristics as outlined in the following list.

| Variety Description Information | |
|---|---|
| Plant Type: | |
| Seed: | |
| Seed Color: | Black |
| Light Dormancy: | Light Not Required |
| Heat Dormancy: | Susceptible |
| Cotyledons: | |
| Shape of Cotyledons: | Broad |
| Shape of Fourth Leaf: | Elongated and Broad |
| Length/Width Index of Fourth Leaf: | 26 |
| Apical Margin: | Entire |
| Basal Margin: | Finely Dentate |
| Undulation: | Flat |
| Green Color: | Dark Green |
| Anthocyanin: | |
| Distribution: | None |
| Rolling: | Absent |
| Cupping: | Uncupped |
| Reflexing: | Lateral Margins |
| Mature Leaves: | |
| Margin: | |
| Incision Depth (Deepest penetration of the margin): | Moderate |

-continued

Variety Description Information

| | |
|---|---|
| Indentation (Finest Division of the Margin): | Crenate |
| Undulation of the Apical Margin: | Moderate |
| Green Color: | Medium Green |
| Anthocyanin Distribution : | None |
| | None |
| Size: | Medium Large |
| Glossiness: | Moderate |
| Blistering: | Slight |
| Leaf Thickness: | Intermediate |
| Trichomes: | Absent |

| | Legend | Pybas 251 | Bonanza |
|---|---|---|---|
| Comparison to Parent Line | | | |
| Characteristic | | | |
| Spread of Frame Leaves | 47 | 48 | 46 |
| Head Diameter (market trimmed with single cup leaf) | 15 | 15 | 15 |
| Head Shape | Round | Round/Bulb | Round |
| Head Size Class | Large | Large | Large |
| Head Count per Carton | 24 | 24 | 24 |
| Head Weight | 795 g | 783 g | 746 g |
| Head Firmness | Firm | Firm | Firm |
| Butt Shape | Round | Round/Point | Round |
| Midrib | Slightly Raised | Raised | Slightly Raised |
| Core (Stem of Market-trimmed Head) | | | |
| Diameter at the base of the Head | 36 mm | 36 mm | 36 mm |
| Ratio of Head Diameter/Core Diameter | 4.16 | 4.16 | 4.16 |
| Core Height from base of Head to Apex | 37 mm | 36 mm | 37 mm |
| Number of Days from First Water Date to Seed Stalk Emergence (Summer condition) | 60 | 60 | 56 |
| Bolting Class | Medium | Medium | Medium |
| Height of Mature Seed Stalk | 102 cm | 116 cm | 86 cm |
| Spread of Bolter Plant Bolter Leaves | 32 | 33 | 33 |
| Margin | Curved | Curved | Curved |
| Color | Med Green | Med Green | Med Green |
| Bolter Habit | | | |
| Terminal Inflorescence | Present | Present | Present |
| Lateral Shoots (above head) | Present | Present | Present |
| Basal Side Shoots | Absent | Absent | Absent |
| Adaptation Regions | Early Salinas | Early Salinas | Early Salinas |
| Growing Season | | | |
| Season | | | |
| Spring area | Salinas Valley | Salinas Valley | Salinas Valley |
| Summer area | Salinas Valley | Salinas Valley | Salinas Valley |
| Fall area | NA | NA | NA |
| Greenhouse: Not tested | NA | NA | NA |

-continued

| | Legend | Pybas 251 | Bonanza |
|---|---|---|---|
| Diseases and Stress Reactions | | | |
| Disease or Stress | | | |
| Virus | NA | NA | NA |
| Big Vein: | Resistant | Susceptible | Resistant |
| Lettuce Mosaic: | NA | NA | NA |
| Cucumber Mosaic: | NA | NA | NA |
| Broad Bean Wilt: | NA | NA | NA |
| Turnip Mosaic: | NA | NA | NA |
| Best Western Yellows: | NA | NA | NA |
| Lettuce Infectious Yellows: | NA | NA | NA |
| Fungi/Bacteria | | | |
| Fungal/Bacterial | | | |
| Corky Root Rot (Pythium Root Rot): | NA | NA | NA |
| Downy Mildew (Races I, IIA, III): | NA | NA | NA |
| Powdery Mildew: | NA | NA | NA |
| Sclerotinia Rot: | NA | NA | NA |
| Bacterial Soft Rot (Pseudomonas spp. & others): Not tested | NA | NA | NA |
| Botrytis (Gray Mold): | NA | NA | NA |
| Other: Corky Root Rot (Rhizomonas suberifaciens): | NA | NA | NA |
| Insects | | | |
| Insects | | | |
| Cabbage Loopers: | NA | NA | NA |
| Root Aphids: | NA | NA | NA |
| Green Peach Aphid: | NA | NA | NA |
| Physiological/Stress | | | |
| Stress | | | |
| Tipburn | Tolerant | NA | NA |
| Heat | NA | NA | NA |
| Drought | NA | NA | NA |
| Cold | Tolerant | Tolerant | Tolerant |
| Salt | NA | NA | NA |
| Post Harvest | | | |
| Characteristic | | | |
| Pink Rib | NA | NA | NA |
| Russet Spotting | NA | NA | NA |
| Rusty Brown Discoloration | NA | NA | NA |
| Internal Rib Necrosis (Blackheart, Gray Rib, Gray Streak) | NA | NA | NA |
| Brown Stain | NA | NA | NA |

Breeding and Selection

The present invention is further directed to the use of Legend lettuce in breeding and selection of new varieties.

A. Breeding

In lettuce breeding, lines are selected for their appropriate characteristics. For example, one line may be selected for bolt tolerance in the fall growing conditions of the desert production locations of California and Arizona or for resistance to Big Vein. Another line may be selected for the size, color and texture of the lettuce head. Crosses are made, for example, to produce a dark green, sure heading iceberg lettuce with improved texture, and size for fall plantings in Yuma, Ariz., and Huron, Calif.

To optimize crossing, it is important to note that lettuce is an obligate self-pollinating species. This means that the pollen is shed before stigma emergence, assuring 100% self-fertilization. Since each lettuce flower is an aggregate of about 10–20 individual florets (typical of the Compositae family), manual removal of the anther tubes containing the pollen may be performed by procedures well known in the art of lettuce breeding.

In addition to manual removal of anther tubes, a modified method of misting to wash the pollen off prior to fertilization may be used to assure crossing or hybridization. About 60–90 min past sunrise, flowers to be used for crossings are selected. The basis for selection are open flowers, with the stigma emerged and the pollen visibly attached to the single stigma (about 10–20 stigma). Using 3–4 pumps of water from a regular spray bottle, the pollen are washed off with enough pressure to dislodge the pollen grains, but not enough to damage the style. Excess water is dried off with clean paper towels. About 30 min later the styles should spring back up and the two lobes of the stigma are visibly open in a "V" shape. Pollen from another variety or donor parent are then introduced by gently rubbing the stigma and style of the donor parent to the maternal parent. Tags with the pertinent information on date and pedigree are then secured to the flowers.

About 2–3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two useful references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907–908 both of which are hereby incorporated by reference in their entirety.

B. Selection

In addition to crossing, selection may be used to isolate lettuce new lettuce lines. In lettuce selection, one or more lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determined if they exhibit the desired characteristics of the originally selected line. Selection work is continued over multiple generations to increase the uniformity of the new line.

IX. DEPOSIT INFORMATION

Applicants have made available to the public without restriction a deposit of at least 2500 seeds of lettuce variety Legend with the American Type Culture Collection (ATCC), Rockville, MD 20852 on Jan. 24, 2001, which has been assigned ATCC number PTA-4009.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

X. EXAMPLES

Example 1: General Trialing Method

I. Set Up

The following steps illustrate the general trialing method of the invention.

1. A trial is set up to compare one or more lines. Parental lines and competing varieties are identified.
2. Primary slots are identified.
3. Necessary accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting

1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance

1. All tested varieties are treated identically. Plants are watered, fertilized, and treated to control pests in the same manner as other lettuce plants in the commercial field.
2. The trial is thinned to separate the plants for optimum growth.

IV. Evaluation

1. Evaluations are done as near to the time of the commercial harvest as possible.
2. The evaluation is conducted "blindly". The evaluator(s) do not have the key to the trial at the time of evaluation.
3. 24 heads of each variety are evaluated.
   a. The frame diameter of 24 random plants are measured to the nearest cm.
   b. 24 mature heads of each variety are cut to the cap leaf.
   c. The heads are carried to an adequate work station
   d. The following measurements are then conducted and recorded:
      1. Each head is weighed to the nearest gram.
      2. The core diameter of each head is measured to the nearest mm.
      3. The heads are then sliced in to halves, discarding 1 half.
      4. The core lengths (from the cut stem to the core tip) are measured to the nearest mm.
      5. The head length (from the cut stem to the cap leaf) is measured to the nearest mm.
      6. The head diameter (at its widest point) is measured to the nearest mm.
      7. The ideal maturity or harvest date is then estimated based on the solidity of the head, the core length and any other physiological characteristics present.
      8. The leaf color is documented using the Munsell Color Charts for Plant Tissue.
   e. From these measurements, an Excel program is used to calculate the averages, the standard deviations and the T-Tests for the compared varieties.

Example 2: Comparative Analysis

Following the procedures of Example 1, Legend iceberg lettuce was compared to various other varieties. Comparative data was obtained and analyzed for different iceberg lettuce lines. Core length, core diameter, head diameter, head length, average head diameter, frame diameter and head weight as provided in the definitions section above and FIG. 1 were compared. The data are presented in Tables 1–13.

Table 1 shows trial data comparing Legend and Bonanza iceberg lettuce varieties.

Table 2 shows trial data comparing Legend and Bonanza iceberg lettuce varieties. Table 3 shows trial data comparing Legend and Bonanza iceberg lettuce varieties. Table 4 shows trial data comparing Legend and Bonanza iceberg lettuce varieties. Table 5 shows trial data comparing Legend and Bonanza iceberg lettuce varieties. Table 6 shows trial data comparing Legend and Bonanza iceberg lettuce varieties. Table 7 shows trial data comparing Legend and Pybas 251 iceberg lettuce varieties. Table 8 shows trial data comparing Pybas 251 and Legend iceberg lettuce varieties. Table 9 shows trial data comparing Legend and Pybas 251 iceberg lettuce varieties. Table 10 shows trial data comparing Legend and Pybas 251 iceberg lettuce varieties. Table 11 shows trial data comparing Legend and Pybas 251 iceberg lettuce varieties. Table 12 shows trial data comparing Sharpshooter and Legend iceberg lettuce varieties. Table 13 shows bolting data comparing Legend, Pybas 251 and Bonanza iceberg lettuce varieties.

TABLE 1

| Trial map #: | | PD0003 | | | Comparison of Head Characteristics | | | | | Maturity Date: | | | | Days to Maturity: | |
|---|---|---|---|---|---|---|---|---|---|---|---|---|---|---|---|
| Wet Date: | | 2/3/ | | Location: Spreckels | | Ranch/Lot: Spreckels/5 | | | 1 Legend | | | 5/7/ | | 94 | |
| Date eval'd: | | 5/8/ | | Grower: C & M Cattle/T & A | | Commercial vMystic | | | 2 Bonanza | | | 5/9/ | | 96 | |
| Sample # | Core length (cm) | | Core diam. (cm) | | Head diam. (cm) | | Head length (cm) | | Avg Head Diameter | | (Avg Head Diam: Core L) | | Frame diam (cm) | | Head wt. (g) | |
| | Legend | Bonanza | Legend | Bonanza | Legend | Bonanza | Legend | Bonanza | Legend | Bonanza | Legend | Bonanza | Legend | Bonanza | Legend | Bonanza |
| 1 | 2.8 | 2.8 | 3.7 | 3.2 | 15.5 | 16.4 | 16.2 | 14.8 | 15.9 | 15.6 | 5.7 | 5.6 | 52 | 49 | 726 | 624 |
| 2 | 5.4 | 3.0 | 3.3 | 3.3 | 18.5 | 14.2 | 16.6 | 15.1 | 17.6 | 14.7 | 3.3 | 4.9 | 51 | 51 | 881 | 555 |
| 3 | 3.2 | 2.8 | 3.6 | 3.5 | 16.0 | 16.4 | 13.6 | 14.2 | 14.8 | 15.3 | 4.6 | 5.5 | 47 | 49 | 687 | 599 |
| 4 | 2.8 | 3.5 | 3.2 | 3.3 | 20.8 | 17.2 | 16.4 | 14.6 | 18.6 | 15.9 | 6.6 | 4.5 | 49 | 47 | 853 | 475 |
| 5 | 5.3 | 3.2 | 3.4 | 3.3 | 16.2 | 14.8 | 15.5 | 15.0 | 15.9 | 14.9 | 3.0 | 4.3 | 44 | 43 | 706 | 498 |
| 6 | 3.6 | 2.8 | 3.5 | 3.5 | 16.5 | 15.1 | 14.7 | 14.2 | 15.6 | 14.7 | 4.3 | 4.6 | 46 | 49 | 764 | 642 |
| 7 | 2.5 | 4.0 | 3.5 | 3.3 | 16.6 | 17.2 | 13.5 | 15.5 | 15.1 | 16.4 | 6.0 | 5.8 | 45 | 44 | 658 | 797 |
| 8 | 4.6 | 3.0 | 3.8 | 3.0 | 16.3 | 16.5 | 14.8 | 18.4 | 15.6 | 17.5 | 3.4 | 4.4 | 47 | 50 | 805 | 705 |
| 9 | 3.8 | 2.9 | 3.0 | 3.0 | 16.3 | 13.8 | 14.3 | 12.7 | 15.0 | 13.3 | 3.9 | 4.4 | 49 | 51 | 880 | 705 |
| 10 | 4.6 | 3.8 | 2.8 | 3.0 | 17.3 | 16.4 | 15.4 | 15.3 | 16.4 | 15.9 | 3.6 | 5.5 | 50 | 47 | 591 | 662 |
| 11 | 5.3 | 3.6 | 3.8 | 3.2 | 15.8 | 19.9 | 14.8 | 17.8 | 15.3 | 18.9 | 2.9 | 5.0 | 47 | 45 | 506 | 552 |
| 12 | 4.5 | 3.2 | 3.4 | 3.5 | 16.3 | 13.5 | 14.4 | 12.8 | 15.4 | 13.2 | 3.4 | 3.7 | 48 | 48 | 889 | 423 |
| 13 | 3.4 | 3.5 | 4.1 | 3.3 | 19.2 | 14.7 | 15.6 | 15.0 | 17.4 | 14.9 | 5.1 | 4.6 | 51 | 48 | 740 | 672 |
| 14 | 5.2 | 2.7 | 3.5 | 3.5 | 15.9 | 13.8 | 14.2 | 13.5 | 15.1 | 13.7 | 2.9 | 3.9 | 52 | 49 | 1027 | 749 |
| 15 | 3.8 | 3.1 | 3.6 | 3.5 | 17.0 | 15.3 | 14.6 | 14.6 | 15.8 | 15.0 | 4.2 | 5.5 | 50 | 48 | 900 | 774 |
| 16 | 4.2 | 3.4 | 3.8 | 3.0 | 16.5 | 15.6 | 14.7 | 15.1 | 15.6 | 15.4 | 3.7 | 5.0 | 50 | 50 | 727 | 790 |
| 17 | 3.8 | 2.8 | 3.2 | 3.3 | 16.3 | 14.9 | 14.2 | 14.2 | 15.3 | 14.6 | 4.0 | 5.2 | 47 | 44 | 631 | 771 |
| 18 | 4.1 | 2.6 | 3.6 | 3.3 | 15.1 | 13.6 | 13.4 | 11.2 | 14.3 | 12.4 | 3.5 | 4.8 | 51 | 48 | 819 | 764 |
| 19 | 3.6 | 3.2 | 3.6 | 3.4 | 16.0 | 14.0 | 15.2 | 15.1 | 15.6 | 14.6 | 4.3 | 4.5 | 50 | 50 | 755 | 698 |
| 20 | 4.2 | 3.1 | 3.4 | 3.2 | 17.1 | 14.1 | 16.3 | 13.8 | 16.7 | 14.0 | 4.0 | 4.5 | 53 | 47 | 723 | 384 |
| 21 | 2.8 | 2.8 | 3.3 | 3.6 | 17.0 | 15.3 | 15.0 | 14.1 | 16.0 | 14.7 | 5.7 | 5.3 | 49 | 46 | 840 | 554 |
| 22 | 3.5 | 2.5 | 3.2 | 3.5 | 15.5 | 14.2 | 14.3 | 14.1 | 14.9 | 14.2 | 4.3 | 5.7 | 52 | 50 | 797 | 586 |
| 23 | 3.0 | 3.6 | 4.0 | 3.3 | 16.2 | 15.1 | 14.8 | 14.0 | 15.5 | 14.6 | 5.2 | 4.0 | 50 | 47 | 760 | 681 |
| 24 | 2.5 | 3.0 | 3.5 | 3.0 | 15.1 | 17.2 | 14.2 | 16.3 | 14.7 | 16.8 | 5.9 | 5.6 | 50 | 47 | 763 | 661 |
| Average | 3.9 | 3.1 | 3.5 | 3.3 | 16.6 | 15.4 | 14.9 | 14.6 | 15.7 | 15.0 | 4.3 | 4.9 | 49.2 | 47.8 | 767.8 | 638.4 |
| Stan dev | 0.90504824 | 0.391185 | 0.300603 | 0.193368 | 1.309656 | 1.532451 | 0.8967635 | 1.496929224 | 0.998032 | 1.409305 | 1.075555579 | 0.605154 | 2.35292 | 2.206299 | 112.1825634 | 116.4959 |
| T test | 0.00006308 | | 0.011662 | | 0.005029 | | 0.5833003 | | 0.047839 | | 0.034134089 | | 0.042327 | | 0.000291098 | |

TABLE 2

Comparison of Head Characteristics

| Trial map #: | SV00085-A | | | | | | | | | | | | | Maturity Date: | | | | |
|---|---|---|---|---|---|---|---|---|---|---|---|---|---|---|---|---|---|---|
| Wet Date: | 3/17/ | | Location: King City | | | | | | Ranch/lot: Commercial Var | | | | Merrill/413 Hallmark | | | 1 Legend | 6/2/ | Days to Maturity: 77 |
| Date evald: | 5/31/ | | Grower: Mission Ranches | | | | | | | | | | | | | 2 Bonanza | 6/4/ | 79 |

| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
|---|---|---|---|---|---|---|---|---|---|---|---|---|---|---|---|---|
| Sample # | Legend | Bonanza | Legend | Bonanza | Legend | Bonanza | Legend | Bonanza | Legend | Bonanza | Legend | Bonanza | Legend | Bonanza | Legend | Bonanza |
| 1 | 3.1 | 2.1 | 3.6 | 3.1 | 18.1 | 13.6 | 13.4 | 13.1 | 15.8 | 13.4 | 5.1 | 6.4 | 47 | 40 | 649 | 438 |
| 2 | 3.1 | 3.0 | 3.7 | 3.6 | 14.3 | 13.8 | 13.2 | 14.8 | 13.8 | 14.3 | 4.4 | 4.8 | 44 | 40 | 525 | 531 |
| 3 | 2.0 | 2.9 | 3.3 | 3.4 | 15.2 | 14.0 | 12.5 | 16.0 | 13.9 | 15.0 | 6.9 | 5.2 | 43 | 45 | 681 | 696 |
| 4 | 4.0 | 2.1 | 3.5 | 3.8 | 17.1 | 14.4 | 14.0 | 13.2 | 15.6 | 13.8 | 3.9 | 6.6 | 46 | 45 | 572 | 427 |
| 5 | 3.6 | 2.0 | 3.3 | 3.1 | 15.4 | 13.0 | 13.5 | 12.8 | 14.5 | 12.9 | 4.0 | 6.1 | 45 | 47 | 564 | 414 |
| 6 | 3.4 | 2.4 | 3.5 | 3.5 | 16.3 | 12.0 | 15.3 | 14.2 | 15.8 | 13.1 | 4.6 | 6.6 | 43 | 44 | 490 | 946 |
| 7 | 3.5 | 2.0 | 3.3 | 3.6 | 15.2 | 13.0 | 12.9 | 13.0 | 14.1 | 13.0 | 4.0 | 5.4 | 43 | 46 | 505 | 456 |
| 8 | 2.9 | 2.5 | 3.3 | 3.1 | 14.5 | 12.1 | 13.6 | 14.0 | 14.1 | 13.1 | 4.8 | 6.5 | 45 | 44 | 583 | 577 |
| 9 | 3.0 | 2.6 | 3.6 | 3.7 | 14.5 | 16.7 | 13.6 | 14.2 | 14.1 | 15.5 | 4.7 | 6.2 | 46 | 45 | 662 | 635 |
| 10 | 3.0 | 2.0 | 3.5 | 3.3 | 14.5 | 16.2 | 14.3 | 14.0 | 14.4 | 15.1 | 4.8 | 5.8 | 47 | 44 | 549 | 511 |
| 11 | 2.3 | 2.7 | 3.0 | 3.2 | 15.2 | 15.7 | 13.1 | 15.0 | 14.2 | 15.4 | 6.2 | 7.7 | 49 | 46 | 592 | 613 |
| 12 | 4.0 | 3.4 | 3.5 | 3.3 | 16.4 | 15.7 | 13.4 | 13.8 | 14.9 | 14.8 | 3.7 | 5.5 | 46 | 42 | 506 | 784 |
| 13 | 2.5 | 2.7 | 3.5 | 3.2 | 16.5 | 15.3 | 13.3 | 15.4 | 14.9 | 15.4 | 6.0 | 4.5 | 48 | 43 | 557 | 636 |
| 14 | 3.2 | 2.6 | 3.5 | 3.6 | 15.5 | 15.4 | 12.6 | 14.2 | 14.1 | 14.8 | 4.4 | 5.5 | 48 | 46 | 586 | 786 |
| 15 | 3.5 | 3.0 | 3.0 | 3.5 | 14.5 | 13.5 | 14.4 | 14.1 | 14.5 | 13.8 | 4.1 | 5.3 | 43 | 46 | 442 | 719 |
| 16 | 2.6 | 2.1 | 3.5 | 3.0 | 14.7 | 15.3 | 13.7 | 12.8 | 14.2 | 14.1 | 5.5 | 4.7 | 45 | 42 | 578 | 629 |
| 17 | 2.6 | 2.7 | 3.7 | 3.3 | 14.0 | 16.5 | 12.8 | 15.7 | 13.4 | 16.1 | 5.2 | 6.0 | 46 | 41 | 503 | 562 |
| 18 | 3.2 | 3.0 | 3.6 | 3.4 | 14.6 | 14.8 | 13.3 | 14.2 | 14.0 | 14.5 | 4.4 | 4.8 | 47 | 46 | 619 | 865 |
| 19 | 3.4 | 3.0 | 3.3 | 3.4 | 13.1 | 14.2 | 14.2 | 12.8 | 13.7 | 13.5 | 4.0 | 4.5 | 47 | 43 | 546 | 574 |
| 20 | 4.0 | 3.2 | 3.5 | 3.5 | 14.0 | 15.5 | 13.5 | 16.7 | 13.8 | 16.1 | 3.4 | 5.0 | 44 | 44 | 654 | 567 |
| 21 | 3.6 | 2.3 | 3.6 | 3.5 | 13.5 | 12.5 | 14.2 | 12.1 | 13.9 | 12.3 | 3.8 | 5.3 | 50 | 48 | 582 | 780 |
| 22 | 2.5 | 2.7 | 3.4 | 3.3 | 15.5 | 15.0 | 14.4 | 14.5 | 15.0 | 14.8 | 6.0 | 5.5 | 43 | 43 | 566 | 650 |
| 23 | 2.6 | 2.6 | 3.5 | 3.2 | 14.2 | 13.5 | 12.7 | 13.2 | 13.5 | 13.4 | 5.2 | 5.1 | 48 | 43 | 563 | 455 |
| 24 | 3.0 | 3.8 | 3.5 | 3.4 | 15.7 | 16.1 | 13.7 | 15.2 | 14.7 | 15.7 | 4.9 | 4.1 | 49 | 45 | 546 | 567 |
| Average | 3.1 | 2.6 | 3.4 | 3.4 | 15.1 | 14.5 | 13.6 | 14.1 | 14.3 | 14.3 | 4.8 | 5.5 | 45.9 | 44.1 | 567.5 | 617.4 |
| Stan dev | 0.545269512 | 0.472658 | 0.181729 | 0.206945 | 1.16413 | 1.394996 | 0.671576 | 1.148352 | 0.6792705 | 1.090429 | 0.869864 | 0.833432208 | 2.145098896 | 2.104171 | 57.83635 | 141.8756 |
| T test | 2.73E-03 | | 2.14E-01 | | 1.05E-01 | | 4.50E-02 | | 9.20E-01 | | 2.36E-03 | | 4.48E-03 | | 1.17E-01 | |

TABLE 3

| Trial map #: | SV00119 | | | | | Comparison of Head Characteristics | | | | | Maturity Date: | | Days to Maturity: | |
|---|---|---|---|---|---|---|---|---|---|---|---|---|---|---|
| Wet Date: | 4/11/ | | Location: Salinas | | | Ranch/lot: | | Cooper/5 | | | 1 Legend | 6/21/ | 71 | |
| Date evald: | 6/20/ | | Grower: Blanco | | | Commercial Var | | Sharpshooter | | | 2 Bonanza | 6/24/ | 74 | |
| Sample | Core length (cm) | | Core diam. (cm) | | Head diam. (cm) | | Head length (cm) | | Avg Head Diameter (cm) | | Avg Head Diam: Core Length | | Frame diam (cm) | | Head wt. (g) | |
| # | Bonanza | Legend | Bonanza | Legend | Bonanza | Legend | Bonanza | Legend | Bonanza | Legend | Bonanza | Legend | Bonanza | Legend | Bonanza | Legend |
| 1 | 4.5 | 3.4 | 3.4 | 3.8 | 3.4 | 14.4 | 15.9 | 14.3 | 9.7 | 14.4 | 2.1 | 4.2 | 49 | 48 | 1042 | 810 |
| 2 | 6.0 | 4.7 | 4.5 | 3.7 | 17.1 | 13.0 | 17.5 | 15.3 | 17.3 | 14.2 | 2.9 | 3.0 | 47 | 46 | 1278 | 953 |
| 3 | 4.7 | 3.0 | 3.5 | 4.0 | 16.5 | 13.1 | 15.5 | 14.0 | 16.0 | 13.6 | 3.4 | 4.5 | 49 | 46 | 1065 | 670 |
| 4 | 2.5 | 3.2 | 4.2 | 3.7 | 15.4 | 13.1 | 14.5 | 13.5 | 15.0 | 13.3 | 6.0 | 4.2 | 51 | 43 | 679 | 798 |
| 5 | 3.6 | 3.0 | 3.9 | 3.5 | 12.6 | 15.4 | 15.6 | 14.6 | 14.1 | 15.0 | 3.9 | 4.7 | 48 | 43 | 1087 | 882 |
| 6 | 3.8 | 3.2 | 3.8 | 3.5 | 17.0 | 15.2 | 15.3 | 14.4 | 16.2 | 14.8 | 4.3 | 4.9 | 49 | 43 | 1186 | 801 |
| 7 | 3.5 | 4.0 | 3.5 | 3.8 | 15.5 | 14.2 | 15.6 | 14.4 | 15.6 | 14.3 | 4.4 | 4.5 | 51 | 42 | 973 | 1016 |
| 8 | 6.0 | 2.7 | 4.5 | 3.8 | 17.6 | 14.7 | 16.1 | 13.8 | 16.9 | 14.3 | 2.8 | 3.6 | 42 | 40 | 700 | 659 |
| 9 | 4.7 | 3.8 | 3.2 | 3.6 | 17.5 | 15.2 | 16.5 | 17.0 | 17.0 | 16.1 | 3.6 | 6.0 | 50 | 42 | 816 | 879 |
| 10 | 4.5 | 3.7 | 3.8 | 3.6 | 17.0 | 14.0 | 15.8 | 13.0 | 16.4 | 13.5 | 3.6 | 3.6 | 51 | 47 | 1194 | 1016 |
| 11 | 4.6 | 3.6 | 3.8 | 3.6 | 16.3 | 15.6 | 14.5 | 14.5 | 15.4 | 15.1 | 3.3 | 4.1 | 51 | 45 | 1229 | 855 |
| 12 | 3.2 | 4.1 | 4.0 | 3.4 | 17.0 | 16.3 | 16.3 | 15.4 | 16.7 | 15.9 | 5.2 | 4.4 | 51 | 46 | 953 | 997 |
| 13 | 4.0 | 2.5 | 3.7 | 3.8 | 15.3 | 14.6 | 16.9 | 12.7 | 16.1 | 13.7 | 4.0 | 3.3 | 50 | 48 | 1105 | 863 |
| 14 | 5.4 | 3.2 | 3.7 | 3.7 | 16.5 | 15.7 | 15.8 | 15.1 | 16.2 | 15.4 | 3.0 | 6.2 | 45 | 47 | 941 | 946 |
| 15 | 5.2 | 2.5 | 3.7 | 3.2 | 16.5 | 15.0 | 16.0 | 14.0 | 16.3 | 14.5 | 3.1 | 4.5 | 46 | 45 | 1132 | 926 |
| 16 | 4.5 | 3.5 | 3.1 | 3.9 | 16.3 | 13.2 | 14.4 | 14.6 | 15.4 | 13.9 | 3.4 | 5.6 | 45 | 43 | 549 | 1139 |
| 17 | 3.7 | 3.4 | 3.5 | 3.9 | 17.1 | 15.4 | 16.3 | 13.7 | 16.4 | 14.6 | 4.4 | 4.3 | 45 | 43 | 963 | 856 |
| 18 | 4.0 | 3.8 | 3.1 | 3.5 | 15.3 | 15.2 | 16.1 | 14.2 | 15.7 | 14.7 | 3.9 | 3.9 | 48 | 46 | 800 | 936 |
| 19 | 3.8 | 3.6 | 3.4 | 3.7 | 17.1 | 15.7 | 16.5 | 14.8 | 16.8 | 15.3 | 4.4 | 4.2 | 46 | 48 | 654 | 1022 |
| 20 | 4.0 | 3.2 | 3.7 | 3.4 | 17.6 | 14.0 | 15.8 | 13.5 | 16.7 | 13.8 | 4.2 | 4.3 | 45 | 39 | 721 | 813 |
| 21 | 4.7 | 3.6 | 3.4 | 3.3 | 16.3 | 14.6 | 14.5 | 13.7 | 15.4 | 14.2 | 3.3 | 3.9 | 45 | 41 | 654 | 1075 |
| 22 | 3.9 | 2.5 | 3.6 | 3.5 | 16.8 | 13.5 | 16.3 | 13.9 | 16.6 | 13.7 | 4.2 | 5.5 | 43 | 45 | 823 | 652 |
| 23 | 4.9 | 3.4 | 3.5 | 3.8 | 16.7 | 13.5 | 14.9 | 13.0 | 15.8 | 13.3 | 3.2 | 3.9 | 47 | 43 | 564 | 846 |
| 24 | 5.0 | 3.4 | 3.3 | 3.6 | 17.0 | 13.9 | 16.0 | 14.3 | 16.5 | 14.1 | 3.3 | 4.1 | 43 | 42 | 690 | 870 |
| Average | 4.4 | 3.4 | 3.7 | 3.6 | 16.5 | 14.5 | 15.7 | 14.2 | 15.8 | 14.4 | 3.8 | 4.4 | 47.4 | 44.1 | 908.3 | 886.7 |
| Standev | 0.837082148 | 0.530176 | 0.374069 | 0.199592 | 2.864918 | 0.967731 | 0.782404 | 0.9107152 | 1.49839135 | 0.77486558 | 0.8230305 | 0.780761122 | 2.856152779 | 2.70131476 | 224.0744 | 125.08281 |
| T Test | | 1.30E-05 | | 8.11E-01 | | 3.13E-02 | | 1.70E-07 | | 1.29E-04 | | 9.34E-03 | | 1.65E-04 | | 6.82E-01 |

TABLE 4

Comparison of Head Characteristics

| Trial map #: | PD00007 | | | | | | | | | | | Maturity Date: | | Days to Maturity: | |
|---|---|---|---|---|---|---|---|---|---|---|---|---|---|---|---|
| Wet Date: | 5/24/ | | Location: Salinas | | Ranch/lot: Martella/6 | | | | | | | 1 Legend | 8/5/ | 73 | |
| Date evald: | 7/27/ | | Grower: Bengard | | CommerciaVenus | | | | | | | 2 Bonanza | 8/7/ | 75 | |

| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
|---|---|---|---|---|---|---|---|---|---|---|---|---|---|---|---|---|
| Sample # | Legend | Bonanza | Legend | Bonanza | Legend | Bonanza | Legend | Bonanza | Legend | Bonanza | Legend | Bonanza | Legend | Bonanza | Legend | Bonanza |
| 1 | 4.3 | 3.9 | 3.2 | 3.1 | 13.0 | 17.1 | 16.0 | 16.5 | 14.5 | 16.8 | 3.4 | 4.3 | 54 | 54 | 956 | 743 |
| 2 | 2.5 | 3.9 | 3.5 | 4.1 | 14.0 | 16.1 | 16.0 | 17.1 | 15.0 | 16.6 | 6.0 | 4.3 | 53 | 55 | 800 | 720 |
| 3 | 3.4 | 4.1 | 3.1 | 3.6 | 14.0 | 11.9 | 14.4 | 17.5 | 14.2 | 14.7 | 4.2 | 3.6 | 48 | 53 | 697 | 861 |
| 4 | 4.1 | 5.1 | 3.0 | 4.1 | 17.3 | 16.5 | 17.2 | 18.1 | 17.3 | 17.3 | 4.2 | 3.4 | 53 | 53 | 949 | 887 |
| 5 | 2.6 | 3.4 | 3.2 | 3.5 | 15.3 | 14.6 | 14.4 | 16.1 | 14.9 | 15.4 | 5.7 | 3.0 | 55 | 55 | 958 | 713 |
| 6 | 4.1 | 2.9 | 3.6 | 3.7 | 17.5 | 16.3 | 17.4 | 15.9 | 17.5 | 16.1 | 4.3 | 4.7 | 57 | 56 | 910 | 812 |
| 7 | 5.3 | 5.9 | 3.2 | 4.1 | 16.6 | 15.3 | 16.1 | 17.5 | 16.4 | 16.4 | 3.1 | 5.7 | 56 | 57 | 837 | 712 |
| 8 | 3.5 | 4.3 | 3.3 | 3.6 | 13.3 | 13.5 | 14.1 | 16.1 | 13.7 | 15.7 | 3.9 | 2.7 | 54 | 56 | 754 | 795 |
| 9 | 4.1 | 3.9 | 3.5 | 3.5 | 16.1 | 14.1 | 16.0 | 16.1 | 16.1 | 14.8 | 3.9 | 3.4 | 51 | 54 | 972 | 796 |
| 10 | 4.1 | 3.9 | 3.4 | 4.1 | 16.5 | 15.5 | 15.6 | 17.1 | 16.1 | 15.6 | 3.9 | 4.0 | 56 | 55 | 828 | 739 |
| 11 | 4.1 | 3.9 | 3.3 | 4.0 | 15.3 | 15.2 | 15.5 | 16.3 | 15.4 | 15.9 | 3.8 | 4.1 | 55 | 56 | 1031 | 777 |
| 12 | 4.3 | 4.1 | 3.1 | 3.6 | 15.2 | 16.1 | 16.1 | 17.6 | 15.7 | 16.4 | 3.6 | 4.2 | 56 | 55 | 665 | 710 |
| 13 | 3.6 | 4.1 | 3.2 | 4.2 | 15.5 | 16.1 | 14.6 | 15.9 | 15.1 | 16.0 | 4.2 | 3.9 | 54 | 57 | 839 | 827 |
| 14 | 4.1 | 4.9 | 3.4 | 4.3 | 15.3 | 15.3 | 16.1 | 17.1 | 15.7 | 16.2 | 3.8 | 4.0 | 53 | 53 | 935 | 772 |
| 15 | 3.6 | 2.9 | 3.3 | 4.4 | 15.3 | 14.3 | 17.0 | 15.9 | 16.2 | 15.1 | 4.5 | 3.1 | 55 | 56 | 911 | 801 |
| 16 | 4.1 | 6.1 | 3.5 | 3.6 | 16.5 | 15.5 | 14.1 | 17.1 | 15.3 | 16.3 | 3.7 | 5.6 | 56 | 55 | 952 | 759 |
| 17 | 3.6 | 4.1 | 3.1 | 3.5 | 16.1 | 15.3 | 14.6 | 17.5 | 15.4 | 16.4 | 4.3 | 4.0 | 55 | 56 | 661 | 665 |
| 18 | 2.6 | 5.2 | 3.2 | 3.4 | 14.1 | 16.5 | 15.2 | 17.6 | 14.7 | 17.1 | 5.6 | 3.3 | 56 | 55 | 828 | 711 |
| 19 | 2.3 | 4.9 | 3.0 | 4.1 | 15.6 | 15.1 | 14.3 | 17.2 | 15.0 | 16.2 | 6.5 | 3.3 | 54 | 57 | 628 | 732 |
| 20 | 3.6 | 3.2 | 3.3 | 3.3 | 14.6 | 16.1 | 15.3 | 15.5 | 15.0 | 15.8 | 4.2 | 4.9 | 56 | 56 | 765 | 815 |
| 21 | 3.6 | 5.1 | 3.1 | 3.6 | 15.3 | 17.5 | 14.1 | 17.9 | 14.7 | 17.7 | 4.1 | 3.5 | 53 | 57 | 632 | 910 |
| 22 | 3.6 | 4.1 | 3.5 | 4.1 | 13.6 | 15.6 | 15.2 | 18.0 | 14.4 | 16.8 | 4.0 | 4.1 | 54 | 53 | 948 | 937 |
| 23 | 3.3 | 5.1 | 3.4 | 3.6 | 15.6 | 15.6 | 16.1 | 18.5 | 15.9 | 17.1 | 4.8 | 3.3 | 53 | 55 | 830 | 711 |
| 24 | 3.6 | 4.5 | 3.3 | 3.6 | 15.5 | 16.5 | 16.1 | 17.1 | 15.8 | 16.8 | 4.4 | 3.7 | 55 | 53 | 833 | 809 |
| Average | 3.7 | 4.3 | 3.3 | 3.8 | 15.3 | 15.5 | 15.5 | 17.0 | 15.4 | 16.2 | 4.3 | 3.9 | 54.3 | 55.1 | 838.3 | 779.8 |
| Stan dev | 0.677377723 | 0.839934 | 0.16807 | 0.349356 | 1.187793 | 1.194553 | 0.997379 | 0.830226 | 0.9002717 | 0.761244 | 0.834898 | 0.755381726 | 1.939296152 | 1.380506 | 118.443 | 69.78429 |
| T test | 5.23E-03 | | 1.06E-07 | | 6.56E-01 | | 1.09E-06 | | 1.36E-03 | | 7.74E-02 | | 9.31E-02 | | 4.25E-02 | |

TABLE 5

Comparison of Head Characteristics

| Trial map #: | SV00168 | | | | | | | | Location: Salinas | | | | | | Ranch/lot: Carr Rch | | | | | | | 1 Legend | | Maturity Date: | | Days to Maturity: | |
|---|---|---|---|---|---|---|---|---|---|---|---|---|---|---|---|---|---|---|---|---|---|---|---|---|---|---|---|
| Wet Date: | 6/8/2001 | | | | | | | | Grower: Francioni | | | | | | Commercia Sharpshooter | | | | | | | 2 Bonanza | | 8/13/2001 | | 66 | |
| Date evald: | 8/10/2001 | | | | | | | | | | | | | | | | | | | | | | | 8/16/2001 | | 69 | |

| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
|---|---|---|---|---|---|---|---|---|---|---|---|---|---|---|---|---|
| Sample # | Legend | Bonanza | Legend | Bonanza | Legend | Bonanza | Legend | Bonanza | Legend | Bonanza | Legend | Bonanza | Legend | Bonanza | Legend | Bonanza |
| 1 | 4.3 | 3.9 | 3.2 | 3.1 | 13.0 | 17.1 | 16.0 | 16.5 | 14.5 | 16.8 | 3.4 | 4.3 | 48 | 52 | 956 | 665 |
| 2 | 3.5 | 3.9 | 3.5 | 4.1 | 14.0 | 16.1 | 16.0 | 17.1 | 15.0 | 16.6 | 4.3 | 4.3 | 50 | 48 | 800 | 711 |
| 3 | 3.4 | 4.1 | 3.1 | 3.6 | 14.0 | 11.9 | 14.4 | 17.5 | 14.2 | 14.7 | 4.2 | 3.6 | 47 | 48 | 697 | 732 |
| 4 | 4.1 | 5.1 | 3.0 | 4.1 | 17.3 | 16.5 | 17.2 | 18.1 | 17.3 | 17.3 | 4.2 | 3.4 | 49 | 47 | 949 | 815 |
| 5 | 3.7 | 3.4 | 3.2 | 3.5 | 15.3 | 14.6 | 14.4 | 16.1 | 14.9 | 15.4 | 4.0 | 4.5 | 43 | 44 | 958 | 910 |
| 6 | 4.1 | 2.9 | 3.6 | 3.7 | 17.5 | 16.3 | 17.4 | 15.9 | 17.5 | 16.1 | 4.3 | 5.6 | 50 | 44 | 910 | 937 |
| 7 | 4.3 | 5.9 | 3.2 | 4.1 | 16.6 | 15.3 | 16.1 | 17.5 | 16.4 | 16.4 | 3.8 | 2.8 | 48 | 44 | 837 | 711 |
| 8 | 3.5 | 4.3 | 3.3 | 3.6 | 13.3 | 15.3 | 14.1 | 16.1 | 13.7 | 15.7 | 3.9 | 3.7 | 45 | 49 | 754 | 809 |
| 9 | 4.2 | 3.9 | 3.5 | 3.5 | 16.1 | 13.5 | 16.0 | 16.1 | 16.1 | 14.8 | 3.8 | 3.8 | 41 | 55 | 972 | 756 |
| 10 | 3.6 | 3.9 | 3.4 | 4.1 | 16.5 | 14.1 | 15.6 | 17.1 | 16.1 | 15.6 | 4.5 | 4.0 | 45 | 48 | 828 | 721 |
| 11 | 3.7 | 3.9 | 3.3 | 4.0 | 15.3 | 15.5 | 15.5 | 16.3 | 15.4 | 15.9 | 4.2 | 4.1 | 49 | 48 | 1031 | 865 |
| 12 | 4.3 | 4.1 | 3.1 | 3.6 | 15.2 | 15.2 | 16.1 | 17.6 | 15.7 | 16.4 | 3.6 | 4.0 | 42 | 48 | 665 | 886 |
| 13 | 3.6 | 4.1 | 3.2 | 4.2 | 15.5 | 16.1 | 14.6 | 15.9 | 15.1 | 16.0 | 4.2 | 3.9 | 45 | 47 | 839 | 710 |
| 14 | 3.9 | 4.9 | 3.4 | 4.3 | 15.3 | 15.3 | 16.1 | 17.1 | 15.7 | 16.2 | 4.0 | 3.3 | 43 | 46 | 935 | 819 |
| 15 | 3.6 | 2.9 | 3.3 | 4.4 | 15.3 | 14.3 | 17.0 | 15.9 | 16.2 | 15.1 | 4.5 | 5.2 | 53 | 51 | 911 | 759 |
| 16 | 4.1 | 6.1 | 3.5 | 3.6 | 16.5 | 15.5 | 14.1 | 17.1 | 15.3 | 16.3 | 3.7 | 2.7 | 50 | 50 | 952 | 801 |
| 17 | 3.6 | 4.1 | 3.1 | 3.5 | 16.1 | 15.3 | 14.6 | 17.5 | 15.4 | 16.4 | 4.3 | 4.0 | 48 | 51 | 661 | 772 |
| 18 | 2.6 | 5.2 | 3.2 | 3.4 | 14.1 | 16.5 | 15.2 | 17.6 | 14.7 | 17.1 | 5.6 | 3.3 | 45 | 49 | 828 | 827 |
| 19 | 2.3 | 4.9 | 3.0 | 4.1 | 15.6 | 15.1 | 14.3 | 17.2 | 15.0 | 16.2 | 6.5 | 3.3 | 42 | 45 | 628 | 710 |
| 20 | 3.6 | 3.2 | 3.3 | 3.3 | 14.6 | 16.1 | 15.3 | 15.5 | 15.0 | 15.8 | 4.2 | 4.9 | 45 | 50 | 765 | 772 |
| 21 | 3.6 | 5.1 | 3.1 | 3.6 | 15.3 | 17.5 | 14.1 | 17.9 | 14.7 | 17.7 | 4.1 | 3.5 | 44 | 48 | 632 | 740 |
| 22 | 3.6 | 4.1 | 3.5 | 4.1 | 13.6 | 15.6 | 15.2 | 18.0 | 14.4 | 16.8 | 4.0 | 4.1 | 47 | 43 | 948 | 795 |
| 23 | 3.3 | 5.1 | 3.4 | 3.6 | 15.6 | 15.6 | 16.1 | 18.5 | 15.9 | 17.1 | 4.8 | 3.3 | 48 | 45 | 830 | 663 |
| 24 | 3.6 | 4.5 | 3.3 | 3.6 | 15.5 | 16.5 | 16.1 | 17.1 | 15.8 | 16.8 | 4.4 | 3.7 | 53 | 42 | 833 | 785 |
| Average | 3.7 | 4.3 | 4.3 | 3.8 | 15.3 | 15.5 | 15.5 | 17.0 | 15.4 | 16.2 | 4.3 | 3.9 | 46.7 | 47.6 | 838.3 | 787.9 |
| Stan dev | 0.484973479 | 0.839934 | 0.839934 | 0.349356 | 1.187793 | 1.194553 | 0.997379 | 0.830226 | 0.9002717 | 0.761244 | 0.643855 | 0.694518061 | 3.331883743 | 3.105628 | 118.443 | 80.61387 |
| T test | 2.22E−03 | | 6.07E−03 | | 6.56E−01 | | 1.09E−06 | | 1.36E−03 | | 5.32E−02 | | 3.29E−01 | | 1.46E−01 | |

TABLE 6

| Trial map #: PDY00027PVP | Location: Gila | | Ranch/lot: | 6/3B | Date evald 3/8/ | | | Maturity Date: | | Days to Maturity: | |
|---|---|---|---|---|---|---|---|---|---|---|---|
| Wet Date: 11/9/ | Grower: Mellon | | Commercial Var: | Bubba | Eval by: JT | | | 1 Legend 3/8/ | | 119 | |
| | | | | | | | | 2 Bonanza 3/16/ | | 127 | |

| | Core length (mm) | | Core diam. (mm) | | Head diam. (mm) | | Head length (mm) | | Avg Head Diameter (mm) | | Avg Head Diam:Core | | Frame diam (cm) | | Head wt. (g) | |
|---|---|---|---|---|---|---|---|---|---|---|---|---|---|---|---|---|
| Sample # | Legend | Bonanza | Legend | Bonanza | Legend | Bonanza | Legend | Bonanza | Legend | Bonanza | Legend | Bonanza | Legend | Bonanza | Legend | Bonanza |
| 1 | 40.0 | 37.0 | 35.0 | 35.0 | 145.0 | 145.0 | 150.0 | 140.0 | 147.5 | 142.5 | 3.7 | 3.9 | 45 | 39 | 1119 | |
| 2 | 39.0 | 33.0 | 30.0 | 40.0 | 160.0 | 150.0 | 145.0 | 130.0 | 152.5 | 140.0 | 3.9 | 4.2 | 40 | 37 | 1199 | |
| 3 | 50.0 | 40.0 | 32.0 | 35.0 | 160.0 | 155.0 | 150.0 | 140.0 | 155.0 | 147.5 | 3.1 | 3.7 | 45 | 40 | 1134 | |
| 4 | 32.0 | 37.0 | 30.0 | 33.0 | 160.0 | 150.0 | 150.0 | 130.0 | 155.0 | 140.0 | 4.8 | 3.8 | 39 | 40 | 632 | |
| 5 | 39.0 | 35.0 | 32.0 | 34.0 | 165.0 | 145.0 | 150.0 | 140.0 | 157.5 | 142.5 | 4.0 | 3.9 | 40 | 39 | 965 | |
| 6 | 41.0 | 32.0 | 34.0 | 40.0 | 166.0 | 150.0 | 150.0 | 140.0 | 158.0 | 145.0 | 3.9 | 4.1 | 42 | 38 | 1087 | |
| 7 | 47.0 | 41.0 | 35.0 | 41.0 | 145.0 | 155.0 | 140.0 | 130.0 | 142.5 | 147.5 | 3.0 | 4.6 | 43 | 39 | 901 | |
| 8 | 41.0 | 40.0 | 37.0 | 42.0 | 160.0 | 150.0 | 155.0 | 140.0 | 157.5 | 145.0 | 3.8 | 3.4 | 40 | 33 | 969 | |
| 9 | 49.0 | 39.0 | 38.0 | 40.0 | 155.0 | 150.0 | 150.0 | 145.0 | 152.5 | 147.5 | 3.1 | 3.7 | 43 | 36 | 1021 | |
| 10 | 40.0 | 31.0 | 35.0 | 39.0 | 160.0 | 150.0 | 150.0 | 140.0 | 155.0 | 145.0 | 3.9 | 3.7 | 42 | 38 | 854 | |
| 11 | 47.0 | 42.0 | 36.0 | 35.0 | 155.0 | 150.0 | 150.0 | 140.0 | 152.5 | 145.0 | 3.2 | 4.7 | 40 | 38 | 897 | |
| 12 | 39.0 | 31.0 | 37.0 | 39.0 | 150.0 | 155.0 | 140.0 | 140.0 | 145.0 | 147.5 | 3.7 | 3.5 | 45 | 39 | 721 | |
| 13 | 42.0 | 42.0 | 30.0 | 41.0 | 150.0 | 153.0 | 140.0 | 140.0 | 150.0 | 146.5 | 3.6 | 3.6 | 43 | 40 | 1058 | |
| 14 | 39.0 | 40.0 | 32.0 | 40.0 | 150.0 | 150.0 | 140.0 | 140.0 | 145.0 | 145.0 | 3.7 | 4.7 | 44 | 39 | 852 | |
| 15 | 40.0 | 33.0 | 36.0 | 35.0 | 160.0 | 145.0 | 145.0 | 140.0 | 152.5 | 137.5 | 3.8 | 3.5 | 45 | | 806 | |
| 16 | 42.0 | 35.0 | 30.0 | 37.0 | 160.0 | 150.0 | 150.0 | 130.0 | 155.0 | 140.0 | 3.7 | 3.8 | 46 | | 958 | |
| 17 | 35.0 | 33.0 | 35.0 | 40.0 | 145.0 | 150.0 | 150.0 | 130.0 | 147.5 | 140.0 | 4.2 | 4.2 | 45 | | 981 | |
| 18 | 39.0 | 32.0 | 34.0 | 41.0 | 150.0 | 140.0 | 140.0 | 120.0 | 145.0 | 130.0 | 3.7 | 4.1 | 34 | | 880 | |
| 19 | 35.0 | 30.0 | 35.0 | 38.0 | 150.0 | 140.0 | 140.0 | 135.0 | 145.0 | 137.5 | 4.1 | 4.6 | 37 | | 1151 | |
| 20 | 43.0 | 39.0 | 33.0 | 40.0 | 150.0 | 160.0 | 150.0 | 140.0 | 150.0 | 150.0 | 3.5 | 3.8 | 39 | | 859 | |
| 21 | 39.0 | 40.0 | 35.0 | 39.0 | 150.0 | 160.0 | 140.0 | 140.0 | 145.0 | 150.0 | 3.7 | 3.8 | 32 | | 1173 | |
| 22 | 49.0 | 31.0 | 34.0 | 40.0 | 165.0 | 150.0 | 150.0 | 130.0 | 157.5 | 140.0 | 3.2 | 4.5 | 40 | | 1077 | |
| 23 | 53.0 | 37.0 | 40.0 | 36.0 | 150.0 | 140.0 | 140.0 | 130.0 | 145.0 | 135.0 | 2.7 | 3.6 | 39 | | 989 | |
| 24 | 40.0 | 35.0 | 35.0 | 39.0 | 150.0 | 150.0 | 130.0 | 125.0 | 140.0 | 132.5 | 3.5 | 3.8 | 34 | | 932 | |
| Average | 41.7 | 36.0 | 34.2 | 38.3 | 155.0 | 149.5 | 145.6 | 135.6 | 150.3 | 142.6 | 3.7 | 4.0 | 40.9 | 38.2 | 967.3 | |
| Stan dev | 5.11321079 | 3.928482 | 2.648489 | 2.595634574 | 6.662544015 | 6.178504 | 5.954994 | 6.309499 | 5.41267969 | 5.603401 | 0.447147 | 0.404747 | 3.843873348 | 1.888368 | 143.5487 | |
| T test | 9.57E-05 | | 1.92E-06 | | 4.50E-03 | | 9.77E-07 | | 1.29E-05 | | 1.07E-02 | | 1.91E-02 | | 2.39E-06 | |

TABLE 7

| Trial map #: | SY00085-A | | Comparison of Head Characteristics | | | | | | Maturity Date: | | Days to Maturity: | |
|---|---|---|---|---|---|---|---|---|---|---|---|---|
| Wet Date: | 3/17/ | | Location: King City | | | | Ranch/lot: Commercial Var | | Merrill/413 Hallmark | | 6/2/ | 77 |
| Date evald: | 5/31/ | | Grower: Mission Ranches | | | | | | | | 6/4/ | 79 |
| | | | | | | | | | 1 Legend | | | |
| | | | | | | | | | 2 Pybas 251 | | | |
| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
| Sample # | Legend | Pybas 251 | Legend | Pybas 251 | Legend | Pybas 251 | Legend | Pybas 251 | Legend | Pybas 251 | Legend | Pybas 251 | Legend | Pybas 251 | Legend | Pybas 251 |
| 1 | 3.1 | 3.2 | 3.6 | 3.3 | 18.1 | 15.1 | 13.4 | 14.5 | 15.8 | 14.8 | 5.1 | 4.6 | 47 | 44 | 649 | 522 |
| 2 | 3.1 | 3.6 | 3.7 | 3.4 | 14.3 | 13.3 | 13.2 | 13.7 | 13.8 | 13.5 | 4.4 | 3.8 | 44 | 45 | 525 | 634 |
| 3 | 2.0 | 3.5 | 3.3 | 3.2 | 15.2 | 14.0 | 12.5 | 14.3 | 13.9 | 14.2 | 6.9 | 4.0 | 43 | 48 | 681 | 615 |
| 4 | 4.0 | 3.0 | 3.5 | 3.0 | 17.1 | 14.7 | 14.0 | 13.4 | 15.6 | 14.1 | 3.9 | 4.7 | 46 | 48 | 572 | 537 |
| 5 | 3.6 | 2.7 | 3.3 | 3.5 | 15.4 | 12.2 | 13.5 | 13.2 | 14.5 | 12.7 | 4.0 | 4.2 | 45 | 48 | 564 | 566 |
| 6 | 3.4 | 2.5 | 3.5 | 3.2 | 16.3 | 14.0 | 15.3 | 14.2 | 15.8 | 14.1 | 4.6 | 5.2 | 43 | 48 | 490 | 551 |
| 7 | 3.5 | 3.2 | 3.3 | 3.4 | 15.2 | 14.0 | 12.9 | 13.9 | 14.1 | 14.0 | 4.0 | 5.6 | 43 | 46 | 505 | 675 |
| 8 | 2.9 | 2.6 | 3.3 | 3.0 | 14.5 | 13.7 | 13.6 | 14.0 | 14.1 | 13.9 | 4.8 | 4.3 | 45 | 45 | 583 | 515 |
| 9 | 3.0 | 2.5 | 3.6 | 3.5 | 14.5 | 15.1 | 13.6 | 13.5 | 14.1 | 14.3 | 4.7 | 5.5 | 46 | 50 | 662 | 471 |
| 10 | 3.0 | 3.2 | 3.5 | 3.4 | 14.5 | 14.4 | 14.3 | 14.4 | 14.4 | 14.4 | 4.8 | 5.8 | 47 | 48 | 549 | 478 |
| 11 | 2.3 | 2.8 | 3.0 | 3.1 | 15.2 | 13.5 | 13.1 | 14.4 | 14.2 | 14.0 | 6.2 | 4.4 | 49 | 45 | 592 | 470 |
| 12 | 4.0 | 3.1 | 3.5 | 3.0 | 16.4 | 15.1 | 13.4 | 14.2 | 14.9 | 14.7 | 3.7 | 5.2 | 46 | 46 | 506 | 515 |
| 13 | 2.5 | 2.6 | 3.5 | 3.3 | 16.5 | 14.8 | 13.3 | 13.7 | 14.9 | 14.3 | 6.0 | 4.6 | 48 | 48 | 557 | 509 |
| 14 | 3.2 | 3.4 | 3.5 | 3.3 | 15.5 | 12.5 | 12.6 | 14.6 | 14.1 | 13.6 | 4.4 | 5.2 | 48 | 48 | 586 | 594 |
| 15 | 3.5 | 2.6 | 3.0 | 3.0 | 14.5 | 14.9 | 14.4 | 12.8 | 14.5 | 13.9 | 4.1 | 4.1 | 43 | 49 | 442 | 572 |
| 16 | 2.6 | 2.1 | 3.5 | 3.0 | 14.7 | 13.4 | 13.7 | 12.3 | 14.2 | 12.9 | 5.5 | 4.9 | 45 | 47 | 578 | 458 |
| 17 | 2.6 | 2.7 | 3.7 | 3.0 | 14.0 | 14.2 | 12.8 | 14.3 | 13.4 | 14.3 | 5.2 | 5.3 | 46 | 49 | 503 | 488 |
| 18 | 3.2 | 2.4 | 3.6 | 3.3 | 14.6 | 15.5 | 13.3 | 14.5 | 14.0 | 15.0 | 4.4 | 6.3 | 47 | 48 | 619 | 631 |
| 19 | 3.4 | 2.6 | 3.3 | 3.4 | 13.1 | 15.4 | 14.2 | 14.4 | 13.7 | 14.9 | 4.0 | 5.7 | 47 | 47 | 546 | 649 |
| 20 | 4.0 | 3.2 | 3.5 | 3.5 | 14.0 | 14.5 | 13.5 | 14.4 | 13.8 | 14.5 | 3.4 | 4.5 | 44 | 47 | 654 | 441 |
| 21 | 3.6 | 3.0 | 3.6 | 3.1 | 13.5 | 15.2 | 14.2 | 13.4 | 13.9 | 14.3 | 3.8 | 4.8 | 50 | 48 | 582 | 533 |
| 22 | 2.5 | 3.0 | 3.4 | 3.4 | 15.5 | 12.3 | 14.4 | 12.6 | 15.0 | 12.5 | 6.0 | 4.2 | 43 | 43 | 566 | 567 |
| 23 | 2.6 | 3.0 | 3.5 | 3.1 | 14.2 | 12.8 | 12.7 | 14.0 | 13.5 | 13.4 | 5.2 | 4.5 | 48 | 45 | 563 | 645 |
| 24 | 3.0 | 3.5 | 3.5 | 3.7 | 15.7 | 13.6 | 13.7 | 15.0 | 14.7 | 14.3 | 4.9 | 4.1 | 49 | 48 | 546 | 600 |
| Average | 3.1 | 2.9 | 3.4 | 3.3 | 15.1 | 14.1 | 13.6 | 13.9 | 14.3 | 14.0 | 4.8 | 4.8 | 45.9 | 47.0 | 567.5 | 551.5 |
| Stan dev | 0.545269512 | 0.393056 | 0.181729 | 0.204257 | 1.16413 | 0.992107 | 0.671576 | 0.67982 | 0.67927058 | 0.657479 | 0.869864 | 0.656840761 | 2.145098896 | 1.744557 | 57.83635 | 67.59599 |
| T test | 1.69E-01 | | 1.27E-03 | | 2.20E-03 | | 9.03E-02 | | 8.70E-02 | | 7.99E-01 | | 6.11E-02 | | 3.83E-01 | |

TABLE 8

| Trial map #: | SV00119 | | Comparison of Head Characteristics | | | | | | Ranch/lot: | Commercial Var | | Cooper/5 Sharpshooter | | | | Maturity Date: | 6/21/ 6/24/ | | Days to Maturity: | 71 74 | |
|---|---|---|---|---|---|---|---|---|---|---|---|---|---|---|---|---|---|---|---|---|---|
| Wet Date: Date evald: | 4/11/ 6/20/ | | | | | | | | Grower: Blanco | | | | | | | 1 Legend 2 Pybas 251 | | | | | |
| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | | | | | | |
| Sample # | Pybas251 | Legend | Pybas251 | Legend | Pybas251 | Legend | Pybas251 | Legend | Pybas251 | Legend | Pybas251 | Legend | Pybas251 | Legend | Pybas251 | Legend | | | | | |
| 1 | 4.6 | 3.4 | 3.1 | 3.8 | 15.0 | 14.4 | 16.2 | 14.3 | 15.6 | 14.4 | 3.4 | 4.2 | 45 | 48 | 564 | 810 | | | | | |
| 2 | 3.9 | 4.7 | 3.5 | 3.7 | 14.0 | 13.0 | 15.7 | 15.3 | 14.9 | 14.2 | 3.8 | 3.0 | 45 | 46 | 1046 | 953 | | | | | |
| 3 | 3.0 | 3.0 | 3.3 | 4.0 | 13.5 | 13.1 | 14.3 | 14.0 | 13.9 | 13.6 | 4.6 | 4.5 | 48 | 46 | 1058 | 670 | | | | | |
| 4 | 3.0 | 3.2 | 3.6 | 3.7 | 15.4 | 13.1 | 15.7 | 13.5 | 15.6 | 13.3 | 5.2 | 4.2 | 41 | 43 | 769 | 798 | | | | | |
| 5 | 2.7 | 3.0 | 3.4 | 3.5 | 14.0 | 15.2 | 14.9 | 14.6 | 14.5 | 15.0 | 5.4 | 4.7 | 40 | 43 | 772 | 882 | | | | | |
| 6 | 2.6 | 3.2 | 3.8 | 3.5 | 14.0 | 14.2 | 16.3 | 14.4 | 15.2 | 14.8 | 5.8 | 4.9 | 41 | 42 | 840 | 801 | | | | | |
| 7 | 3.5 | 4.0 | 3.8 | 3.8 | 15.2 | 14.7 | 15.5 | 14.4 | 15.4 | 14.3 | 4.4 | 4.5 | 44 | 40 | 755 | 1016 | | | | | |
| 8 | 5.0 | 2.7 | 4.0 | 3.8 | 14.0 | 15.2 | 16.5 | 13.8 | 15.3 | 16.1 | 3.1 | 3.6 | 46 | 40 | 810 | 659 | | | | | |
| 9 | 4.5 | 3.8 | 3.4 | 3.6 | 16.4 | 14.7 | 15.0 | 17.0 | 15.7 | 13.5 | 3.5 | 6.0 | 47 | 42 | 705 | 879 | | | | | |
| 10 | 3.8 | 3.7 | 3.6 | 3.6 | 13.0 | 14.0 | 15.6 | 13.0 | 14.3 | 13.5 | 3.8 | 3.6 | 40 | 47 | 709 | 1016 | | | | | |
| 11 | 4.0 | 3.6 | 3.6 | 3.6 | 17.0 | 15.6 | 17.4 | 14.5 | 17.2 | 15.1 | 4.3 | 4.1 | 50 | 45 | 1008 | 855 | | | | | |
| 12 | 3.5 | 4.1 | 3.7 | 3.4 | 14.7 | 16.3 | 15.5 | 15.4 | 15.1 | 15.9 | 4.3 | 4.4 | 45 | 46 | 758 | 997 | | | | | |
| 13 | 4.0 | 2.5 | 3.2 | 3.8 | 16.7 | 14.6 | 17.3 | 12.7 | 17.0 | 13.7 | 4.3 | 3.3 | 45 | 48 | 687 | 863 | | | | | |
| 14 | 4.0 | 3.2 | 4.0 | 3.7 | 13.9 | 15.7 | 15.0 | 15.1 | 14.5 | 15.4 | 3.6 | 6.2 | 46 | 47 | 987 | 946 | | | | | |
| 15 | 3.5 | 2.5 | 3.5 | 3.2 | 16.5 | 15.0 | 15.7 | 14.0 | 16.1 | 14.5 | 4.6 | 4.5 | 44 | 45 | 944 | 926 | | | | | |
| 16 | 3.5 | 3.5 | 4.0 | 3.9 | 16.7 | 13.2 | 15.7 | 14.6 | 16.2 | 13.9 | 4.6 | 5.6 | 41 | 43 | 647 | 1139 | | | | | |
| 17 | 3.0 | 3.4 | 3.5 | 3.9 | 13.9 | 15.4 | 16.1 | 13.7 | 15.0 | 14.6 | 5.0 | 4.3 | 49 | 46 | 1015 | 856 | | | | | |
| 18 | 3.7 | 3.8 | 3.4 | 3.5 | 14.2 | 15.2 | 14.8 | 14.2 | 14.5 | 14.7 | 3.9 | 3.9 | 43 | 43 | 1076 | 936 | | | | | |
| 19 | 2.9 | 3.6 | 3.6 | 3.7 | 16.0 | 15.7 | 15.4 | 14.8 | 15.7 | 15.3 | 5.4 | 4.2 | 42 | 46 | 875 | 1022 | | | | | |
| 20 | 3.3 | 3.2 | 3.4 | 3.4 | 13.5 | 14.0 | 15.5 | 13.5 | 14.5 | 13.8 | 4.4 | 4.3 | 43 | 48 | 671 | 813 | | | | | |
| 21 | 3.1 | 3.6 | 3.5 | 3.3 | 14.0 | 14.6 | 14.0 | 13.7 | 14.0 | 14.2 | 4.5 | 3.9 | 47 | 39 | 1051 | 1075 | | | | | |
| 22 | | 2.5 | 3.5 | 3.5 | | 13.5 | | 13.9 | 0.0 | 13.7 | | 5.5 | 43 | 41 | 687 | 652 | | | | | |
| 23 | | 3.4 | 3.8 | 3.8 | | 13.9 | | 13.0 | 0.0 | 13.3 | | 3.9 | 42 | 45 | 550 | 846 | | | | | |
| 24 | | 3.4 | | 3.6 | | 14.5 | | 14.3 | 0.0 | 14.1 | | 4.1 | | 43 | 650 | 870 | | | | | |
| Average | 3.6 | 3.4 | 3.6 | 3.6 | 14.8 | 14.5 | 15.6 | 14.2 | 13.3 | 14.4 | 4.4 | 4.4 | 44.1 | 42 | 818.1 | 886.7 | | | | | |
| Stan dev | 0.6389087 | 0.530176 | 0.235869 | 0.199592 | 1.25079 | 0.967731 | 0.843744 | 0.910715 | 5.21290162 | 0.774866 | 0.721332 | 0.780761122 | 2.842483095 | 2.701315 | 166.8183 | 125.0828 | | | | | |
| T test | 2.54E−01 | | 1.93E−01 | | 3.43E−01 | | 4.15E−06 | | 3.33E−01 | | 9.55E−01 | | 1.00E+00 | | 1.14E−01 | | | | | | |

TABLE 9

Comparison of Head Characteristics

| | | |
|---|---|---|
| Trial map #: PD00007 | | |
| Wet Date: 5/24/ | Location: Salinas | Ranch/lot: Martella/6 | Maturity Date: | Days to Maturity: |
| Date eval'd: 7/27/ | Grower: Bengard | CommerciaVenus | 1 Legend 7/25/ | 1 Legend 62 |
| | | | 2 Pybas 251 7/27/ | 2 Pybas 251 64 |

| Sample # | Core length (cm) Legend | Core length (cm) Pybas 251 | Core diam. (cm) Legend | Core diam. (cm) Pybas 251 | Head diam. (cm) Legend | Head diam. (cm) Pybas 251 | Head length (cm) Legend | Head length (cm) Pybas 251 | Avg Head Diameter (cm) Legend | Avg Head Diameter (cm) Pybas 251 | Avg Head Diam:Core Legend | Avg Head Diam:Core Pybas 251 | Frame diam (cm) Legend | Frame diam (cm) Pybas 251 | Head wt. (g) Legend | Head wt. (g) Pybas 251 |
|---|---|---|---|---|---|---|---|---|---|---|---|---|---|---|---|---|
| 1 | 4.3 | 5.1 | 3.2 | 4.1 | 13.0 | 16.5 | 16.0 | 17.0 | 14.5 | 16.8 | 3.4 | 3.3 | 54 | 58 | 956 | 907 |
| 2 | 2.5 | 3.9 | 3.5 | 4.3 | 14.0 | 13.5 | 16.0 | 15.2 | 15.0 | 14.4 | 6.0 | 3.7 | 53 | 55 | 800 | 758 |
| 3 | 3.4 | 3.9 | 3.1 | 3.9 | 14.0 | 15.2 | 14.4 | 17.1 | 14.2 | 16.2 | 4.2 | 4.1 | 48 | 54 | 697 | 837 |
| 4 | 4.1 | 4.9 | 3.0 | 3.5 | 17.3 | 16.0 | 17.2 | 16.3 | 17.3 | 16.2 | 4.2 | 3.3 | 53 | 55 | 949 | 898 |
| 5 | 2.6 | 5.1 | 3.2 | 4.3 | 15.3 | 16.5 | 14.4 | 16.9 | 14.9 | 16.7 | 5.7 | 3.4 | 55 | 54 | 958 | 1141 |
| 6 | 4.1 | 2.9 | 3.6 | 4.5 | 17.5 | 14.5 | 17.4 | 14.5 | 17.5 | 14.5 | 4.3 | 2.8 | 57 | 56 | 910 | 1122 |
| 7 | 5.3 | 3.9 | 3.2 | 4.1 | 16.6 | 14.3 | 16.1 | 15.9 | 16.4 | 15.1 | 3.1 | 5.2 | 56 | 54 | 837 | 881 |
| 8 | 3.5 | 5.1 | 3.3 | 4.3 | 13.3 | 14.1 | 14.1 | 18.1 | 13.7 | 16.1 | 3.9 | 4.1 | 54 | 57 | 754 | 814 |
| 9 | 4.1 | 4.3 | 3.5 | 4.0 | 16.1 | 15.6 | 16.0 | 16.1 | 16.1 | 15.9 | 3.9 | 3.1 | 51 | 56 | 972 | 1046 |
| 10 | 4.1 | 5.6 | 3.4 | 4.1 | 16.5 | 15.1 | 15.6 | 19.9 | 16.1 | 17.5 | 3.9 | 4.1 | 56 | 56 | 828 | 875 |
| 11 | 4.1 | 5.9 | 3.3 | 4.2 | 15.3 | 15.6 | 15.5 | 16.1 | 15.4 | 15.9 | 3.8 | 2.8 | 55 | 55 | 1031 | 738 |
| 12 | 4.3 | 4.1 | 3.1 | 4.3 | 15.2 | 16.1 | 16.1 | 16.9 | 15.7 | 16.5 | 3.6 | 2.8 | 56 | 57 | 665 | 839 |
| 13 | 3.6 | 5.1 | 3.2 | 4.1 | 15.5 | 14.9 | 14.6 | 16.9 | 15.1 | 15.9 | 4.2 | 3.9 | 54 | 56 | 839 | 837 |
| 14 | 4.1 | 4.9 | 3.4 | 3.9 | 15.5 | 16.0 | 16.1 | 15.5 | 15.7 | 15.8 | 3.8 | 3.1 | 53 | 55 | 935 | 852 |
| 15 | 3.6 | 4.1 | 3.3 | 3.8 | 15.3 | 15.5 | 17.0 | 16.1 | 16.2 | 15.8 | 4.5 | 3.2 | 55 | 56 | 911 | 857 |
| 16 | 4.1 | 4.2 | 3.5 | 4.1 | 16.5 | 16.1 | 14.1 | 15.9 | 15.3 | 16.0 | 3.7 | 3.9 | 56 | 56 | 952 | 841 |
| 17 | 3.6 | 4.3 | 3.1 | 3.9 | 16.1 | 17.5 | 14.6 | 17.1 | 15.4 | 17.3 | 4.3 | 4.0 | 55 | 58 | 661 | 934 |
| 18 | 2.6 | 3.9 | 3.2 | 3.5 | 14.1 | 13.5 | 15.2 | 14.1 | 14.7 | 13.8 | 5.6 | 3.5 | 56 | 53 | 828 | 919 |
| 19 | 2.3 | 4.3 | 3.0 | 4.5 | 15.6 | 16.1 | 14.3 | 17.2 | 15.0 | 16.7 | 6.5 | 3.9 | 54 | 54 | 628 | 1030 |
| 20 | 3.6 | 3.9 | 3.3 | 3.9 | 14.6 | 15.2 | 15.3 | 16.9 | 15.0 | 16.1 | 4.2 | 3.9 | 56 | 57 | 765 | 1029 |
| 21 | 3.6 | 4.3 | 3.1 | 4.1 | 15.3 | 16.1 | 14.1 | 18.1 | 14.7 | 17.1 | 4.1 | 4.0 | 53 | 53 | 632 | 1035 |
| 22 | 3.6 | 3.1 | 3.5 | 4.2 | 13.6 | 15.1 | 15.2 | 15.5 | 14.4 | 15.3 | 4.0 | 4.9 | 54 | 55 | 948 | 768 |
| 23 | 3.3 | 3.9 | 3.4 | 4.3 | 15.6 | 16.1 | 16.1 | 15.9 | 15.9 | 16.0 | 4.8 | 4.1 | 53 | 53 | 830 | 901 |
| 24 | 3.7 | 4.4 | 3.3 | 4.3 | 15.5 | 16.1 | 16.1 | 16.5 | 15.8 | 16.3 | 4.4 | 3.7 | 55 | 56 | 833 | 907 |
| Average | 3.7 | 4.4 | 3.3 | 4.1 | 15.3 | 15.5 | 15.4 | 16.5 | 15.4 | 16.0 | 4.3 | 3.7 | 54.3 | 55.4 | 838.3 | 906.9 |
| Stan dev | 0.677377723 | 0.71281 | 0.16807 | 0.260295 | 1.187793 | 0.976091 | 0.997379 | 1.212727 | 0.9002717 | 0.891503 | 0.834898 | 0.608194 | 1.939296152 | 1.46888 | 118.443 | 108.8329 |
| T test | 7.97E−04 | | 8.44E−17 | | 5.89E−01 | | 2.90E−03 | | 2.73E−02 | | 4.67E−03 | | 2.82E−02 | | 4.22E−02 | |

TABLE 10

Comparison of Head Characteristics

| Trial map #: | SY00168 | | | | | | Ranch/lot: | Carr Rch | | Maturity Date: | | 8/13/ | Days to Maturity: | 66 |
|---|---|---|---|---|---|---|---|---|---|---|---|---|---|---|
| Wet Date: | 6/8/ | | Location: Salinas | | | | Commercia | Sharpshooter | | | | 8/13/ | | 66 |
| Date evald: | 8/10/ | | Grower: Francioni | | | | | | | 1 Legend | | | | |
| | | | | | | | | | | 2 Pybas251 | | | | |

| | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
|---|---|---|---|---|---|---|---|---|---|---|---|---|---|---|---|---|
| Sample # | Legend | Pybas 251 | Legend | Pybas 251 | Legend | Pybas 251 | Legend | Pybas 251 | Legend | Pybas 251 | Legend | Pybas 251 | Legend | Pybas 251 | Legend | Pybas 251 |
| 1 | 4.3 | 3.0 | 3.2 | 3.2 | 13.0 | 15.5 | 16.0 | 17.1 | 14.5 | 16.3 | 3.4 | 5.4 | 48 | 46 | 828 | 848 |
| 2 | 2.5 | 3.0 | 3.5 | 3.5 | 14.0 | 15.2 | 16.0 | 15.6 | 15.0 | 15.4 | 6.0 | 5.1 | 50 | 52 | 950 | 686 |
| 3 | 3.4 | 3.6 | 3.1 | 3.0 | 14.0 | 14.3 | 14.4 | 15.7 | 14.2 | 15.0 | 4.2 | 4.2 | 47 | 53 | 840 | 535 |
| 4 | 4.1 | 3.2 | 3.0 | 3.6 | 17.3 | 14.5 | 17.2 | 15.4 | 17.3 | 15.0 | 4.2 | 4.7 | 49 | 51 | 949 | 419 |
| 5 | 2.6 | 2.9 | 3.2 | 3.5 | 15.3 | 14.4 | 14.4 | 13.9 | 14.9 | 14.2 | 5.7 | 4.4 | 43 | 49 | 958 | 1091 |
| 6 | 4.1 | 5.0 | 3.6 | 3.2 | 17.5 | 15.2 | 17.4 | 13.9 | 17.5 | 14.6 | 4.3 | 5.0 | 50 | 48 | 910 | 665 |
| 7 | 5.3 | 2.9 | 3.2 | 3.7 | 16.6 | 16.1 | 16.1 | 17.0 | 16.4 | 16.6 | 3.1 | 3.3 | 48 | 52 | 837 | 760 |
| 8 | 3.5 | 2.7 | 3.3 | 3.2 | 13.3 | 18.0 | 14.1 | 15.9 | 13.7 | 17.0 | 3.9 | 5.8 | 45 | 53 | 754 | 553 |
| 9 | 4.1 | 3.7 | 3.5 | 3.4 | 16.1 | 15.6 | 16.0 | 15.3 | 16.1 | 15.5 | 3.9 | 5.7 | 41 | 53 | 972 | 792 |
| 10 | 4.1 | 3.0 | 3.4 | 3.1 | 16.5 | 13.2 | 15.6 | 15.5 | 16.1 | 14.4 | 3.9 | 3.9 | 45 | 52 | 956 | 637 |
| 11 | 4.1 | 5.3 | 3.3 | 3.0 | 15.3 | 15.2 | 15.5 | 16.5 | 15.4 | 15.9 | 3.8 | 5.3 | 49 | 47 | 952 | 490 |
| 12 | 4.3 | 3.0 | 3.1 | 3.6 | 15.2 | 15.4 | 16.1 | 16.9 | 15.7 | 16.2 | 3.6 | 3.0 | 42 | 53 | 665 | 813 |
| 13 | 3.6 | 2.5 | 3.2 | 3.4 | 15.5 | 15.3 | 14.6 | 13.2 | 15.1 | 14.3 | 4.2 | 4.8 | 45 | 49 | 839 | 991 |
| 14 | 4.1 | 3.6 | 3.4 | 3.2 | 15.3 | 14.6 | 16.1 | 16.2 | 15.7 | 15.4 | 3.8 | 6.2 | 43 | 54 | 935 | 812 |
| 15 | 3.6 | 3.2 | 3.3 | 3.2 | 15.3 | 13.6 | 17.0 | 16.0 | 16.2 | 14.8 | 4.5 | 4.1 | 53 | 53 | 911 | 938 |
| 16 | 4.1 | 3.4 | 3.5 | 3.0 | 16.5 | 15.0 | 14.1 | 14.5 | 15.3 | 14.8 | 3.7 | 4.6 | 50 | 46 | 952 | 791 |
| 17 | 3.6 | 4.1 | 3.1 | 3.1 | 16.1 | 13.2 | 14.6 | 16.3 | 15.4 | 14.8 | 4.3 | 3.6 | 48 | 54 | 661 | 1003 |
| 18 | 2.6 | 4.5 | 3.2 | 2.7 | 14.1 | 16.0 | 15.2 | 17.2 | 14.7 | 16.6 | 5.6 | 3.7 | 45 | 54 | 828 | 866 |
| 19 | 2.3 | 2.8 | 3.0 | 3.5 | 15.6 | 16.5 | 14.3 | 15.4 | 15.0 | 16.0 | 6.5 | 5.7 | 42 | 54 | 628 | 794 |
| 20 | 3.6 | 2.7 | 3.3 | 2.9 | 14.6 | 14.7 | 15.3 | 14.9 | 15.0 | 14.8 | 4.2 | 5.5 | 45 | 53 | 765 | 755 |
| 21 | 3.6 | 3.2 | 3.1 | 3.2 | 15.3 | 13.3 | 14.1 | 14.4 | 14.7 | 13.9 | 4.1 | 4.3 | 44 | 48 | 632 | 1006 |
| 22 | 3.6 | 3.7 | 3.5 | 3.0 | 13.6 | 14.6 | 15.2 | 15.8 | 14.4 | 15.2 | 4.0 | 4.1 | 47 | 53 | 948 | 710 |
| 23 | 3.3 | 3.0 | 3.4 | 3.4 | 15.6 | 12.5 | 16.1 | 14.8 | 15.9 | 13.7 | 4.8 | 4.6 | 48 | 53 | 830 | 981 |
| 24 | 3.6 | 4.2 | 3.3 | 3.2 | 15.5 | 14.3 | 16.1 | 16.4 | 15.8 | 15.4 | 4.4 | 3.7 | 53 | 52 | 833 | 766 |
| Average | 3.7 | 3.4 | 3.3 | 3.2 | 15.3 | 14.8 | 15.5 | 15.6 | 15.4 | 15.2 | 4.3 | 4.6 | 46.7 | 51.3 | 847.2 | 779.3 |
| Stan dev | 0.677377723 | 0.732031 | 0.16807 | 0.250072 | 1.187793 | 1.205392 | 0.997379 | 1.074305 | 0.9002717 | 0.892196 | 0.834898 | 0.858916534 | 3.331883743 | 2.648489 | 111.822444 | 174.0313 |
| T test | 2.41E-01 | | 5.32E-01 | | 1.95E-01 | | 7.50E-01 | | 4.92E-01 | | 2.62E-01 | | 2.50E-06 | | 1.14E-01 | |

TABLE 11

| Trial map #: | PDY00027PVP | Location: | Gila | Ranch/lot: | | Date evald: | 3/8/ | | Maturity Date: | | |
|---|---|---|---|---|---|---|---|---|---|---|---|
| Wet Date: | 11/9/ | Grower: | Mellon | Commercial Var: | Bubba | Eval by: | JT | | 1 Legend | 3/8/ | |
| | | | | | | | | | 2 Pybas 251 | 3/20/ | |

| Sample | Core length (mm) | | Core diam. (mm) | | Head diam. (mm) | | Head length (mm) | | Avg Head Diameter (mm) | | Avg Head Diam:Core Length | | Frame diam (mm) | | Days to Matu |
|---|---|---|---|---|---|---|---|---|---|---|---|---|---|---|---|
| # | Legend | Pybas 251 | Legend | Pybas 251 | Legend | Pybas 251 | Legend | Pybas 251 | Legend | Pybas 251 | Legend | Pybas 251 | Legend | Pybas 251 | |
| 1 | 40.0 | 40.0 | 35.0 | 36.0 | 145.0 | 150.0 | 150.0 | 160.0 | 147.5 | 155.0 | 3.7 | 3.9 | 45 | 42 | 119 |
| 2 | 39.0 | 49.0 | 30.0 | 40.0 | 160.0 | 160.0 | 145.0 | 145.0 | 152.5 | 152.5 | 3.9 | 3.1 | 40 | 43 | 131 |
| 3 | 50.0 | 34.0 | 32.0 | 41.0 | 160.0 | 160.0 | 150.0 | 150.0 | 155.0 | 155.0 | 3.1 | 4.6 | 45 | 39 | |
| 4 | 32.0 | 32.0 | 30.0 | 42.0 | 160.0 | 165.0 | 150.0 | 150.0 | 155.0 | 157.5 | 4.8 | 4.9 | 39 | 42 | |
| 5 | 39.0 | 40.0 | 32.0 | 40.0 | 165.0 | 155.0 | 150.0 | 150.0 | 157.5 | 152.5 | 4.0 | 4.8 | 40 | 39 | |
| 6 | 41.0 | 35.0 | 34.0 | 39.0 | 166.0 | 140.0 | 150.0 | 150.0 | 158.0 | 145.0 | 3.9 | 3.6 | 42 | 33 | |
| 7 | 47.0 | 30.0 | 35.0 | 37.0 | 145.0 | 150.0 | 140.0 | 140.0 | 142.5 | 145.0 | 3.0 | 4.1 | 43 | 42 | |
| 8 | 41.0 | 49.0 | 37.0 | 36.0 | 160.0 | 155.0 | 155.0 | 150.0 | 157.5 | 152.5 | 3.8 | 5.1 | 40 | 41 | |
| 9 | 49.0 | 32.0 | 38.0 | 40.0 | 155.0 | 140.0 | 150.0 | 130.0 | 152.5 | 135.0 | 3.1 | 2.8 | 43 | 40 | |
| 10 | 40.0 | 35.0 | 35.0 | 39.0 | 160.0 | 130.0 | 150.0 | 140.0 | 155.0 | 135.0 | 3.9 | 4.2 | 42 | 39 | |
| 11 | 47.0 | 40.0 | 36.0 | 41.0 | 155.0 | 170.0 | 150.0 | 160.0 | 152.5 | 165.0 | 3.2 | 4.7 | 40 | 47 | |
| 12 | 39.0 | 40.0 | 37.0 | 39.0 | 150.0 | 160.0 | 140.0 | 160.0 | 145.0 | 160.0 | 3.7 | 4.0 | 45 | 45 | |
| 13 | 42.0 | 41.0 | 30.0 | 40.0 | 160.0 | 150.0 | 140.0 | 165.0 | 150.0 | 157.5 | 3.6 | 3.9 | 43 | 43 | |
| 14 | 39.0 | 49.0 | 32.0 | 40.0 | 160.0 | 160.0 | 140.0 | 150.0 | 150.0 | 155.0 | 3.7 | 3.8 | 44 | 40 | |
| 15 | 40.0 | 40.0 | 36.0 | 39.0 | 160.0 | 150.0 | 145.0 | 150.0 | 152.5 | 150.0 | 3.8 | 3.1 | 45 | 39 | |
| 16 | 42.0 | 30.0 | 30.0 | 38.0 | 160.0 | 150.0 | 150.0 | 145.0 | 155.0 | 147.5 | 3.7 | 3.7 | 46 | 38 | |
| 17 | 35.0 | 31.0 | 35.0 | 41.0 | 145.0 | 170.0 | 150.0 | 160.0 | 147.5 | 165.0 | 4.2 | 5.3 | 45 | 37 | |
| 18 | 39.0 | 55.0 | 34.0 | 38.0 | 150.0 | 165.0 | 140.0 | 150.0 | 145.0 | 157.5 | 3.7 | 2.9 | 34 | 40 | |
| 19 | 35.0 | 40.0 | 35.0 | 39.0 | 150.0 | 145.0 | 140.0 | 130.0 | 145.0 | 137.5 | 4.1 | 3.4 | 37 | 43 | |
| 20 | 43.0 | 35.0 | 33.0 | 40.0 | 150.0 | 140.0 | 150.0 | 140.0 | 150.0 | 140.0 | 3.5 | 4.0 | 39 | 41 | |
| 21 | 39.0 | 49.0 | 35.0 | 39.0 | 150.0 | 170.0 | 140.0 | 170.0 | 145.0 | 170.0 | 3.7 | 3.5 | 32 | 43 | |
| 22 | 49.0 | 35.0 | 34.0 | 38.0 | 165.0 | 150.0 | 150.0 | 135.0 | 157.5 | 142.5 | 3.2 | 4.1 | 40 | 42 | |
| 23 | 53.0 | 35.0 | 40.0 | 37.0 | 150.0 | 150.0 | 140.0 | 125.0 | 145.0 | 137.5 | 2.7 | 3.9 | 39 | 44 | |
| Average | 41.7 | 39.0 | 34.2 | 39.0 | 155.0 | 154.4 | 145.6 | 147.7 | 150.3 | 151.0 | 3.7 | 4.0 | 40.9 | 41.0 | |
| Stan dev | 5.113211079 | 6.9030554 | 2.648489 | 1.680558051 | 6.66254402 | 9.703484358 | 5.954994 | 11.79343652 | 5.41267969 | 9.750046451 | 0.447146893 | 0.680911891 | 3.843873 | 2.89646211 | |
| T test | 1.35E-01 | | 1.72E-09 | | 7.83E-01 | | 4.44E-01 | | 7.57E-01 | | 6.91E-02 | | 8.99E-01 | | |

TABLE 12

Comparison of Head Characteristics

| Trial map #: | SV00119 | | | | | | | | | | | | | | |
|---|---|---|---|---|---|---|---|---|---|---|---|---|---|---|---|
| Wet Date: | 4/11/ | | | Location: | Salinas | | Ranch/lot: | Cooper/5 | | | Maturity Date: | | Days to Maturity: | | |
| Date evald: | 6/20/ | | | Grower: | Blanco | | Commercial Var | Sharpshooter | | | 1 Sharpshoot | 6/21/ | 71 | | |
| | | | | | | | | | | | 2 Legend | 6/24/ | 74 | | |

| Sample | Core length (cm) | | Core diam. (cm) | | Head diam. (cm) | | Head length (cm) | | Avg Head Diameter (cm) | | Avg Head Diam:Core Le | | Frame diam (cm) | | Head wt. (g) | |
|---|---|---|---|---|---|---|---|---|---|---|---|---|---|---|---|---|
| # | Sharpshooter | Legend | Sharp-shoot | Legend | Sharp-shoot | Legend | Sharpshoot | Legend | Sharpshooter | Legend | Sharpshoot | Legend | Sharpshooter | Legend | Sharpshoot | Legend |
| 1 | 4.4 | 3.4 | 3.5 | 3.8 | 16.2 | 14.4 | 15.0 | 14.3 | 15.6 | 14.4 | 3.5 | 4.2 | 47 | 48 | 1026 | 810 |
| 2 | 4.7 | 4.7 | 3.7 | 3.7 | 14.5 | 13.0 | 16.0 | 15.3 | 15.3 | 14.2 | 3.2 | 3.0 | 41 | 46 | 1152 | 953 |
| 3 | 6.3 | 3.0 | 3.6 | 4.0 | 18.3 | 13.1 | 18.7 | 14.0 | 18.5 | 13.6 | 2.9 | 4.5 | 43 | 46 | 930 | 670 |
| 4 | 5.5 | 3.2 | 3.5 | 3.7 | 15.2 | 13.1 | 14.4 | 13.5 | 14.8 | 13.3 | 4.2 | 4.2 | 43 | 43 | 982 | 798 |
| 5 | 5.1 | 3.0 | 3.6 | 3.5 | 16.1 | 15.4 | 16.5 | 14.6 | 16.3 | 15.0 | 2.7 | 4.7 | 42 | 43 | 864 | 882 |
| 6 | 4.0 | 3.2 | 3.6 | 3.5 | 14.9 | 15.2 | 13.3 | 14.4 | 14.1 | 14.8 | 3.2 | 4.9 | 45 | 42 | 940 | 801 |
| 7 | 4.6 | 4.0 | 3.9 | 3.8 | 16.2 | 14.2 | 14.9 | 14.4 | 15.6 | 14.3 | 3.5 | 4.5 | 45 | 40 | 740 | 1016 |
| 8 | 4.4 | 2.7 | 3.6 | 3.8 | 17.5 | 14.7 | 14.9 | 13.8 | 16.2 | 14.3 | 3.4 | 4.5 | 45 | 40 | 931 | 659 |
| 9 | 5.0 | 3.8 | 3.7 | 3.6 | 15.5 | 15.2 | 15.4 | 17.0 | 15.5 | 16.1 | 3.7 | 3.6 | 46 | 42 | 858 | 879 |
| 10 | 4.7 | 3.7 | 3.5 | 3.6 | 16.4 | 14.0 | 15.5 | 13.0 | 16.0 | 13.5 | 3.1 | 6.0 | 49 | 47 | 903 | 1016 |
| 11 | 5.2 | 3.6 | 3.6 | 3.6 | 15.7 | 15.6 | 15.2 | 14.5 | 15.5 | 15.1 | 3.4 | 3.6 | 46 | 45 | 1058 | 855 |
| 12 | 5.0 | 4.1 | 3.9 | 3.4 | 18.0 | 16.3 | 14.7 | 15.4 | 16.4 | 15.9 | 3.0 | 4.1 | 45 | 46 | 1111 | 997 |
| 13 | 5.0 | 2.5 | 3.8 | 3.8 | 14.6 | 14.6 | 14.9 | 12.7 | 14.8 | 13.7 | 3.3 | 4.4 | 47 | 48 | 912 | 863 |
| 14 | 4.5 | 3.2 | 3.8 | 3.7 | 15.0 | 15.7 | 14.5 | 15.1 | 14.8 | 15.4 | 3.0 | 3.3 | 46 | 47 | 978 | 946 |
| 15 | 5.9 | 2.5 | 3.8 | 3.2 | 15.0 | 15.0 | 14.7 | 14.0 | 14.9 | 14.5 | 3.3 | 6.2 | 47 | 45 | 910 | 926 |
| 16 | 4.8 | 3.5 | 3.4 | 3.9 | 15.3 | 13.2 | 16.2 | 14.6 | 15.8 | 13.9 | 3.3 | 4.5 | 45 | 43 | 1007 | 1139 |
| 17 | 6.5 | 3.4 | 3.5 | 3.9 | 16.0 | 15.4 | 16.5 | 13.7 | 16.3 | 14.6 | 2.5 | 5.6 | 45 | 43 | 931 | 856 |
| 18 | 5.0 | 3.8 | 3.2 | 3.5 | 16.2 | 15.2 | 16.0 | 14.2 | 16.1 | 14.7 | 3.2 | 4.3 | 48 | 46 | 1059 | 936 |
| 19 | 6.0 | 3.6 | 3.7 | 3.7 | 15.0 | 15.7 | 14.8 | 14.8 | 14.9 | 15.3 | 2.5 | 3.9 | 46 | 48 | 1042 | 1022 |
| 20 | 4.0 | 3.2 | 3.5 | 3.4 | 15.0 | 14.0 | 14.9 | 13.5 | 15.3 | 13.8 | 3.8 | 4.2 | 49 | 39 | 923 | 813 |
| 21 | 4.1 | 3.6 | 3.6 | 3.3 | 16.3 | 14.6 | 14.1 | 13.7 | 15.2 | 14.2 | 3.7 | 4.3 | 46 | 41 | 995 | 1075 |
| 22 | 5.0 | 2.5 | 3.5 | 3.5 | 15.6 | 13.5 | 15.5 | 13.9 | 15.6 | 13.7 | 3.1 | 3.9 | 44 | 45 | 1042 | 652 |
| 23 | 4.5 | 3.4 | 4.0 | 3.8 | 15.4 | 13.5 | 16.2 | 13.0 | 15.8 | 13.3 | 3.5 | 5.5 | 45 | 43 | 854 | 846 |
| 24 | 5.0 | 3.4 | 3.8 | 3.6 | 16.7 | 13.9 | 15.0 | 14.3 | 15.9 | 14.1 | 3.2 | 3.9 | 41 | 42 | 1033 | 870 |
| Average | 5.0 | 3.4 | 3.6 | 3.6 | 15.9 | 14.5 | 15.4 | 14.2 | 15.6 | 14.4 | 3.2 | 4.4 | 45.3 | 44.1 | 965.9 | 886.7 |
| Stan dev | 0.673515544 | 0.530176 | 0.18133 | 0.199592 | 1.007328 | 0.967731 | 1.056647 | 0.910715 | 0.84831194 | 0.7748661 | 0.374302 | 0.780761122 | 2.151844507 | 2.701315 | 92.61341 | 125.0828 |
| T test | 7.55E-12 | | 1.00E+00 | | 2.46E-05 | | 2.91E-04 | | 4.02E-06 | | 1.92E-08 | | 1.05E-01 | | 1.63E-02 | |

TABLE 13

Bolting Habit

| Block: | 2000 26 | Date Eval: 8/25/ Eval By: DG | Area: | SJV |
|---|---|---|---|---|
| Variety: | Legend | Wet Date: 5/11/ | | |

| | Height mature Seed Stalk | | | Width of Seed Head | | |
|---|---|---|---|---|---|---|
| Plant Number | Legend | Pybas 251 | Bonanza | Legend | Pybas 251 | Bonanza |
| 1 | 101 | 118 | 86 | 27 | 37 | 32 |
| 2 | 93 | 124 | 85 | 26 | 40 | 32 |
| 3 | 90 | 120 | 82 | 30 | 37 | 30 |
| 4 | 103 | 118 | 82 | 32 | 44 | 31 |
| 5 | 101 | 121 | 90 | 39 | 34 | 28 |
| 7 | 107 | 110 | 87 | 30 | 38 | 30 |
| 8 | 102 | 114 | 90 | 35 | 43 | 30 |
| 9 | 100 | 119 | 89 | 29 | 33 | 33 |
| 10 | 98 | 109 | 89 | 36 | 31 | 33 |
| 11 | 94 | 110 | 82 | 29 | 30 | 31 |
| 12 | 99 | 116 | 86 | 35 | 30 | 37 |
| 13 | 102 | 112 | 87 | 32 | 27 | 34 |
| 14 | 96 | 118 | 84 | 31 | 29 | 33 |
| 15 | 104 | 118 | 90 | 30 | 26 | 33 |
| 16 | 109 | 116 | 94 | 32 | 28 | 38 |
| 17 | 100 | 118 | 81 | 34 | 30 | 38 |
| 18 | 110 | 119 | 93 | 34 | 22 | 30 |
| 19 | 104 | 100 | 94 | 33 | 34 | 33 |
| 20 | 109 | 123 | 96 | 35 | 31 | 28 |
| Average | 101.6 | 116 | 87.55 | 31.6 | 33 | 32.5 |
| Standard Dev | 5.6976449 | 5.57248881 | 4.465953 | 3.775266 | 5.712406 | 2.964705 |
| T-Test | | 2.5436E−07 | 3.41E−11 | | 0.415924 | 0.758568 |

| | Bolting Date | | |
|---|---|---|---|
| | Legend | Pybas 251 | Bonanza |
| Days to Maturity | 7/10/ #VALUE! | 7/10/ #VALUE! | 7/6/ #VALUE! |

| Bolting Leaves Shape: Straight or curved | | |
|---|---|---|
| Legend | Pybas 251 | Bonanza |
| Curved | Curved | Curved |

| Margin Smooth or Dentate | | |
|---|---|---|
| Legend | Pybas 251 | Bonanza |
| Serrated | Serrated | Serrated |

| Color Lt, Med, Dark | | |
|---|---|---|
| Legend | Pybas 251 | Bonanza |
| Medium Green | Medium Gre | Medium green |

| Terminal Inflorescence Yes, No | | |
|---|---|---|
| Legend | Pybas 251 | Bonanza |
| Yes | Yes | yes |

| Seed Color | | |
|---|---|---|
| Legend | Pybas 251 | Bonanza |
| Black | Black | Black |

TABLE 13-continued

| Bolting Habit | Legend | Pybas 251 | Bonanza |
|---|---|---|---|
| Lateral shoots btwn head and seed stalk | No | Yes | Yes |
| Lateral shoots above seed head | Yes | yes | Yes |
| Basal shoots | No | No | No |

*T-Test compares Variety to: Legend

Legend is an iceberg lettuce variety that combines the large heading and frame characteristics of its parent variety Pybas 251 with the big vein resistance of Bonanza. By combining these traits, Legend provides the commercial lettuce grower/shipper with an improved heading variety that overcomes the yield loss associated with symptoms caused by big vein during the winter and early spring planting period in the Salinas Valley.

The combination of these two varieties produced an increased tolerance to tip burn as well, an additional and unexpected trait increasing the varieties' distinctness and value. With the increased heat tolerance Legend has a broader adaptability in terms of planting dates and locations.

Legend most closely resembles its seed bearing parent Pybas 251. Legend is clearly distinguishable by the following characteristics. Pybas 251 tends to form slightly elongated heads, and has extremely long wrapper leaves that grow upright and completely cover the head. Legend is similar in size, but the heads are more spherical, and the growth habit of the wrapper leaves is flatter, more open and slightly shorter. Both varieties are only slightly savoyed or even smooth, characteristic of Salinas type varieties. Additional distinctions are evident by the plants growth habit in seed production. Pybas 251 is a considerably larger plant, both significantly taller, and has a larger seed head. The most evident distinction between these two varieties is Legends resistance to big vein.

In comparison to the parental variety Bonanza, Legend has a smoother leaf texture, more open growing habit and a wider range of adaptability due to its tolerance to tip burn and bolting tendencies. During the February and March plantings, the core length of Legend is longer than Bonanza. As the plantings continue through out the spring and into early summer, the core length of Legend remains constant, while Bonanza has a longer core length. This is also evident in summer seed production statistics, where Bonanza bolts at day 56 and Legend at day 60. During the February and March plantings, Legend produces a larger head and frame diameter. As the plantings continue through the spring and summer, in warmer conditions, Bonanza out grows Legend and produces a larger head and frame.

Legend produces a consistently similar product from the winter plantings through the early summer plantings, with little change in performance in terms of head, frame and core size. Bonanza is effected more severely by the warmer conditions as evident by the longer cores and larger heading measured in trials under more heat stress.

Legend matures, forming a commercially acceptable lettuce head, on average 2–3 days earlier than either Pybas 251 or Bonanza in trials conducted in the Salinas Valley.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

We claim:

1. Lettuce seed having ATCC Accession Number PTA-4009.

2. A lettuce plant produced by growing the seed of claim 1.

3. A lettuce plant having all the physiological and morphological characteristics of the lettuce plant of claim 2.

4. A method of making an $F_1$ hybrid lettuce plant consisting of crossing Legend as a first lettuce parent plant with a second lettuce parent plant, wherein Legend is grown from the seed of claim 1; harvesting the resultant $F_1$ hybrid seed; and growing an $F_1$ hybrid seed into an $F_1$ hybrid lettuce plant.

5. Pollen of the plant of claim 2.

6. An ovule of the plant of claim 2.

7. Tissue culture of the plant of claim 2.

* * * * *